United States Patent
Camden

(10) Patent No.: US 6,362,207 B1
(45) Date of Patent: *Mar. 26, 2002

(54) METHODS OF TREATING VIRAL INFECTIONS WITH BENZIMIDAZOLES

(75) Inventor: James Berger Camden, West Chester, OH (US)

(73) Assignee: The Procter & Gamble Company, Cincinnati, OH (US)

(*) Notice: Subject to any disclaimer, the term of this patent is extended or adjusted under 35 U.S.C. 154(b) by 0 days.

This patent is subject to a terminal disclaimer.

(21) Appl. No.: 09/748,651

(22) Filed: Dec. 22, 2000

Related U.S. Application Data

(60) Division of application No. 09/264,942, filed on Mar. 9, 1999, now Pat. No. 6,262,093, which is a continuation-in-part of application No. 08/927,550, filed on Sep. 6, 1997, now Pat. No. 5,880,144, which is a division of application No. 08/771,193, filed on Dec. 20, 1996, now Pat. No. 5,767,138, which is a division of application No. 08/420,914, filed on Apr. 12, 1995, now abandoned, said application No. 09/264,942, is a continuation-in-part of application No. 09/081,384, filed on May 19, 1998, now abandoned, and a continuation-in-part of application No. 09/081,627, filed on May 19, 1998, now abandoned.

(51) Int. Cl.⁷ ..................... A61K 31/53; A61K 31/495
(52) U.S. Cl. ..................... 514/365; 514/397; 514/398; 424/450; 424/451; 424/464; 424/486
(58) Field of Search .................. 514/365, 397, 514/398; 424/450, 451, 468, 486

(56) References Cited

U.S. PATENT DOCUMENTS

| | | | |
|---|---|---|---|
| 2,933,502 A | 4/1960 | Klopping | 260/299 |
| 3,010,968 A | 11/1961 | Loux | 260/309.2 |
| 3,370,957 A | 2/1968 | Wagner et al. | 99/90 |
| 3,499,761 A | 3/1970 | Dersch | 96/66.5 |
| 3,541,213 A | 11/1970 | Klopping | 424/273 |
| 3,669,969 A | 6/1972 | Lunn | 260/256.4 |
| 3,738,995 A | 6/1973 | Adams et al. | 260/309.2 |
| 3,881,014 A | 4/1975 | Regel et al. | 424/273 |
| 3,956,262 A | 5/1976 | Heyes et al. | 424/140 |

(List continued on next page.)

FOREIGN PATENT DOCUMENTS

| | | |
|---|---|---|
| BE | 667158 | 11/1965 |
| EP | 617968 A1 | 10/1994 |
| FR | 2155888 | 5/1973 |
| GB | 1123317 | 8/1968 |
| JP | 7 277 956 | 10/1995 |
| WO | WO 94/04541 | 3/1994 |
| WO | WO 96/32103 | 10/1996 |
| WO | WO 96/32104 | 10/1996 |
| WO | WO 96/32107 | 10/1996 |
| WO | WO 96/32115 | 10/1996 |
| WO | WO 96/40119 | 12/1996 |
| WO | WO 96/40120 | 12/1996 |
| WO | WO 96/40122 | 12/1996 |
| WO | WO 97/05870 | 2/1997 |
| WO | WO 97/05872 | 2/1997 |
| WO | WO 97/05873 | 2/1997 |
| WO | WO 98/32440 | 7/1998 |
| WO | WO 98/51303 | 11/1998 |
| WO | WO 98/51304 | 11/1998 |
| WO | WO 99/59585 | 11/1999 |

OTHER PUBLICATIONS

Atassi, et al., "R17934–NSC 238159: A New Antitumor Drug", pp. 599–607, (1975), Europ. J. Cancer, vol. 11, Pergamon Press.

Aur, "Treatment of Parasitic Infestation in Children with Malignant Neoplasms" pp. 129–131,(1971), The Journal of Pediatrics, vol. 78, No. 1, Mosby, Inc.

Bissery, et al., "Docetaxel in Vivo Combination Chemotherapy", pp. 3–16, (1995), Seminars in Oncology, vol. 22, No. 6–S13, W. B. Saunders Company.

Brabender, et al., "The Effects of Methyl [5–(2–Thienylcarbonyl)–1H–benzimidazol–2–yl]carbamate, (R 17934;NSC 238159), a New Antitumoral Drug Interfering with Microtubules", pp. 905–916, (1976), Cancer Research, vol. 36, American Association of Cancer Research.

Brown, et al., "Antiparasitic Drugs. IV. 2–(4'–Thiazolyl-)–Benzimidazole, A New Anthelmintic", pp. 1764–1765, (1961), J. American Chemistry Society., Am. Chem. Soc.

Carter et al., "Drug–Tumor Interactions", pp. 362–365, (1981), Chemotherapy of Cancer, 2$^{nd}$ Ed., John Wiley & Sons, NY, NY.

(List continued on next page.)

Primary Examiner—Frederick Krass
(74) Attorney, Agent, or Firm—Bart S. Hersko; Leonard W. Lewis

(57) ABSTRACT

This invention is a method of treating cancer, both carcinomas and sarcomas, and viral infections, in particular HIV through the administration of a pharmaceutical composition containing a benzimidazole derivative. The composition is also claimed. The benzimidazole derivative is selected from the group consisting of:

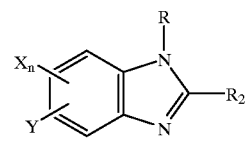

wherein X is hydrogen, halogen, alkyl of less than 7 carbon atoms or alkoxy of less than 7 carbon atoms; n is a positive integer of less than 4; Y is hydrogen, chlorine, nitro, methyl, ethyl or oxychloro; R is hydrogen, alkylaminocarbonyl wherein the alkyl group has from 3 to 6 carbon atoms, or an alkyl group of from 1 to 8 carbon atoms and $R_2$ is 4-thiazolyl, $NHCOOR_1$ wherein $R_1$ is aliphatic hydrocarbon of less than 7 carbon atoms, prodrugs, pharmaceutically acceptable salts and mixtures thereof and a pharmaceutically acceptable carrier.

41 Claims, No Drawings

U.S. PATENT DOCUMENTS

| | | | |
|---|---|---|---|
| 4,046,906 A | 9/1977 | Frensch et al. | 424/273 |
| 4,731,366 A | 3/1988 | Munro et al. | 514/278 |
| 4,814,329 A | 3/1989 | Harsanyi et al. | 514/211 |
| 5,098,923 A | 3/1992 | Karjalainen et al. | 514/396 |
| 5,114,951 A | 5/1992 | King | 514/290 |
| 5,149,527 A | 9/1992 | Weisenthal | 424/85.2 |
| 5,290,801 A | 3/1994 | Higley et al. | 514/395 |
| 5,310,748 A | 5/1994 | Wilde et al. | 514/395 |
| 5,329,012 A | 7/1994 | Anderson | 548/318.5 |
| 5,364,875 A | 11/1994 | Wilde | 514/375 |
| 5,434,163 A * | 7/1995 | Edlind | 514/310 |
| 5,629,341 A | 5/1997 | Camden | |
| 5,656,615 A | 8/1997 | Camden | |
| 5,665,713 A | 9/1997 | Camden | |
| 5,665,751 A | 9/1997 | Camden | |
| 5,767,138 A | 6/1998 | Camden | |
| 5,770,616 A | 6/1998 | Camden | |
| 5,840,742 A | 11/1998 | Camden | |
| 5,854,231 A | 12/1998 | Camden | |
| 5,872,142 A | 2/1999 | Camden | |
| 5,880,144 A * | 3/1999 | Camden | 514/397 |
| 5,900,429 A | 5/1999 | Camden | |
| 5,902,804 A | 5/1999 | Camden | |
| 5,908,855 A | 6/1999 | Camden | |
| 5,929,099 A | 7/1999 | Camden | |
| 5,932,604 A | 8/1999 | Camden | |
| 5,932,609 A | 8/1999 | Camden | |
| 5,958,950 A | 9/1999 | Padia et al. | |
| 6,025,377 A | 2/2000 | Camden | |
| 6,077,862 A | 6/2000 | Camden | |
| 6,090,796 A | 7/2000 | Camden | |
| 6,110,953 A | 8/2000 | Camden | |
| 6,136,835 A | 10/2000 | Camden | |
| 6,177,460 B1 | 1/2001 | Camden | |
| 6,211,177 B1 | 4/2001 | Sperl et al. | |

OTHER PUBLICATIONS

Carter, "2–(α–Hydroxybenzyl)–Benzimidazole", pp. 277–346, (1975), Selective Inhibitors of Viral Functions, CRC Press, Cleveland, OH.

Chimeno, Process for the perparation of alkyl N'–alkylcarbomoyl–N–(2–benizimidazolyl) carbamates, (1987), Chemical Abstracts 107:39817, American Chemical Society.

Delatour, et al.,"Embryotoxic and Antimitotic Properties in the Benzimidazole Series", pp. 505–515, (1976),Therapie, vol. 31, No. 4, John Libbey & Co., Ltd., (English translation thereof).

DuPont, "'Benlate' Fungicide", pp. 1–9, (1994), Material Safety Data Sheet, DuPont.

Elgebaly, et al., "Reversal of gamma–Radiation–Induced Leukogenesis in Mice by Immunomodulation with Thiabendazole and Dinitrofluorobenzene", pp. 811–815 (1985), Chemical Abstracts 102:217569, American Chemical Society.

Elgebaly, et al., "Reversal of gamma–Radiation–Induced Leukemogenesis in Mice by Immunomodulation with Thiabendazole and Dinitrofluorobenzene", pp. 811–815 (1985), J. Natl. Cancer Inst., Oxford University Press.

Friedman, et al., "Interaction of Anthelmintic and Benzimidazole Derivatives with Bovine Brain Tubulin", pp. 605–614, (1978), Biochimica et Biophysica Acta, Elsevier/North–Holland Biomedical Press.

Georgopapadakov, et al., "Human Mycoses: Drugs and Targets for Emerging Pathogens", pp. 371–373, (1994), Science, vol. 264, American Association for the Advancement of Science.

Ghannoum, et al., "Combinations of antifungal and antineoplastic drugs with interactive effects on inhibition of yeast growth", pp. 308–320, (1990), Chemical Abstracts 113:112365, American Chemical Society.

Graubaum, et al., "Acylation of Hetrocycles with Carbonic Acid Derivatives", pp. 809–815, (1982), Chemical Abstracts 98:52877, American Chemical Society.

Grenda, et al., "Novel Preparation of Benzimidazles from N–Arylamidines. New Synthesis of Thiabendazole", pp. 259–261, (1965), Journal Organic Chemistry, vol. 30, Academic Chemical Society.

Katiyar, et al., "Antiprotozol activities of benzimidazoles and correlations with beta–tubuli sequence", pp. 2086–2090, (1994), Chemical Abstracts 121:175012z, American Chemical Society.

Lacey, et al., "Activity of Benzimidazole Carnmates against L1210 Mouse Leukaemia Cells"Correlation with in vtiro Tubulin Polymerization Assay, pp. 3603–3605 (1985), Biochemical Pharmacology, vol. 34, No. 19, Pergamon Press Ltd.

Lacey, et al., "Structure–Activity Relationships of Benzimidazole Carbmates as Inhibitors of Mammalian Tubulin, in vitro", pp. 1073–1077 (1985), Biochemical Pharmacology, No. 7, Pregamon Press Ltd.

Lacey, et al., "The Role of the Cytoskeletal Protein, Tubulin, in the Mode of Action and Mechanism or Drug Resisteance to Benzimidazoles", pp. 885–936, (1988), International Journal for Parasitology, vol. 18, No. 7, Pergamon Press Ltd.

Lapras, et al. "Experimental Study of the Potential Anticancerous Properties of Parbendazole (SKF 29044)", pp. 379–397, (1975), Bull. Soc. Sci. Vet. et Med. comparee, Lyon, vol. 77, No. 6, Societe des Sciences veterinaries et de Medecine comparee de Lyon, (in French) —and English translation thereof.

Lessnau et al., "Disseminated Strongyloides stercoralis in Human Immunodeficiency Virus–infected Patients", pp. 119–122, (1993), Chest, vol. 104, American College of Chest Physicians.

Lovett, "Immunomodulating Effects of Thiabendazole: Immunotherapeutic Efficacy in the Treatment of Murine Fibrosarcoa", pp. 5315–5316, (1979), Dissertation Abstracts International, *Health Science, Immunology*, vol. 39, No. 11, U M I.

Lundy, et al., "Chemoimmunotherapy of a murine fibrosarcoma: critical factors for success of combined modality therapy", pp. 339–345,(1997), Chemical Abstracts 87:161659, American Chemical Society.

Lundy, et al., "Immunomodulation with Thiabendazole: A Review of Immunologic Properties and Efficacy in Combined Modality Cancer Therapy", pp. 1955–1962, (1978), Cancer Treatments Reports, vol. 62, No. 11, U.S. Department of Health, Education, and Welfare.

Lundy, et al., "Thiabendazole: A New Immunopotentiator Effective in Therapy of Murine Fibrosarcoma", pp. 132–134, (1976), Surgical Forum, vol. 27, No. 62, American College of Surgeons.

Marinovich, et al., "Mixture of Benomyl, Primiphos–Methyl, Dimethoate, Diazinon and Azinphos–Methyl Affect Protein Synthesis in HL–60 Cells Differently", pp. 173–185, (1994), Toxicol., vol. 94, Elsevier Science Ireland Ltd.

Menzel, et al., "Effects of some systemic fungicides on viral multiplication", pp. 353–362, (1979), Chemical Abstracts 92:123231, American Chemical Society.

The Merck Index, Twelfth Edition, "7943: 'Procodazole", p. 1333, and "9877: 'Triprolidine", pp. 1660–1661, (1996), Merck Research Laboratories.

The Merck Index, Eighth Edition, "Thiabendazole", p. 1035, (1968), Merck & Co., Inc.
Nene, et al., "Systemic Fungicides", pp. 208–386, (1993), Fungicides in Plant Disease Control, Third Edition, Ch. 9, International Science Publisher.
Private Communication to Dr. Von Hoff from National Institute of Health, National Cancer Society (Sep. 18, 1995).
Ram, et al., "Synthesis and Biological Activity of Certain Alkyl 5-(Alkoxycarbonyl)-1H-Benzimidazole-2-carbmates and Realted Derivatives: A New Class of Potential Antineoplastic and Antifilarial Agents", pp. 539–547, (1992), Journal of Medicinal Chemistry, vol. 35, No. 3, American Chemical Society.
Stedman's Medical Dictionary, 24th Edition, "Leukemia", pp. 777–778, (1983), Williams & Wilkins.
Tanneberg, et al., "Substituted Benzimidazolecarbmates", p. 7 (1985), Chemical Abstracts 102:24617, American Chemical Society.
Teicher, et al., "Potentiation of Cytotxic Therapies by TNP–470 and Minocycline in Mice Bearing EMT–6 Mammary Carcinoma", pp. 227–236, (1995), Breast Cancer Research and Treatment, vol. 36, Kluwer Academic Publishers.
Thomson, "Fungicides", pp. 154, 121, 123, (1993–1994 Revision), Agricultural Chemicals Book IV, Thomson Publications.
Vergieva, "Carbendazim teratogenic activity of rats", pp. 333–339, (1982) Chemical Abstracts 98:66765, American Chemical Society.
Pending Application of Camden, Ser. No. 09/264,942, filed Mar. 9, 1999. (5638D2C).
Pending Application of Camden, Ser. No. 09/375,173, filed Aug. 16, 1999. (5702CR).
Pending Application of Camden, Ser. No. 09/469,389, filed Dec. 22, 1999. (5703D2C).
Pending Application of Camden, Ser. No. 09/360,499, filed Jul. 26, 1999. (5781D).
Pending Application of Camden, Ser. No. 08/674,182, filed Jul. 16, 1996, CPA filed Feb. 10, 1999. (5782).
Pending Application of Camden, Ser. No. 09/371,457, filed Aug. 10, 1999. (5784R).
Pending Application of Camden, Ser. No. 09/371,459, filed Aug. 10, 1999. (5784R2).
Pending Application of Camden, Ser. No. 09/364,021, filed Jul. 30, 1999. (5785D2)
Pending Application of Camden, Ser. No. 09/312,948, filed May 17, 1999. (5786D).
Pending Application of Camden, Ser. No. 09/394,383, filed Sep. 10, 1999. (5786DR).
Pending Application of Camden, Ser. No. 09/218,884, filed Dec. 22, 1998. (6496D).
Pending Application of Camden, Ser. No. 08/857,811, filed May 16, 1997, CPA filed Jul. 28, 1999. (6643).
Pending Application of Camden, Ser. No. 09/312, 949, filed May 17, 1999. (7161R).
Pending Application of Camden, Ser. No. 09/374,717, filed Aug. 13, 1999. (7719)
Pending Application of Camden, Ser. No. 09/462,243, filed Jan. 05, 2000 (6642).
Pending Application of Camden, Ser. No. 09/552,408, filed Apr. 19, 2000. (6496D2).
Pending Application of Camden, Ser. No. 09/552,825, filed Apr. 20, 2000. (6643D2).
Pending Application of Camden, Ser. No. 09/552,820, filed Apr. 20, 2000. (6643D3).
Pending Application of Camden, Ser. No. 09/560,059, filed Apr. 27, 2000. (5781D3).
Pending Application of Camden, Ser. No. 09/603,040, filed Jun. 26, 2000. (5781DC).
Pending Application of Camden, Ser. No. 09/791,986, filed Apr. 28, 2000. (8068).
Pending Application of Camden, Ser. No. 09/562,709, filed Apr. 28, 2000. (8069).
Pending Application of Camden, Ser. No. 09/602,170, filed Jun. 22, 2000. (5783C2).
Pending Application of Camden, Ser. No. 09/603,322, filed Jun. 26, 2000. (5781D2).
Pending Application of Camden, Ser. No. 09/618,990, filed Jul. 18, 2000. (5702CRD).
Pending Application of Camden, Ser. No. 09/639,188, filed Aug. 15, 2000 (5784R2D).
Pending Application of Camden, Ser. No. 09/640,148, filed Aug. 16, 2000 (5784R2C).
Pending Application of Camden, Ser. No. 09/645,708, filed Aug. 24, 2000 (5785D2RD).
Pending Application of Camden, Ser. No. 09/645,427, filed Aug. 24, 2000 (5785D2RD2).
Pending Application of Camden, Ser. No. 09/640,920, filed Aug. 17, 2000 (7161R2).
Pending Application of Camden, Ser. No. 09/640,918, filed Aug. 17, 2000 (7161R3).
Pending Application of Camden, Ser. No. 09/640,919, filed Aug. 17, 2000 (7161R4).
Pending Application of Camden, Ser. No. 09/676,407, filed Sep. 29, 2000 (6643R).
Pending Application of Camden, Ser. No. 09/676,034, filed Sep. 29, 2000 (6643R2).
Pending Application of Camden, Ser. No. 09/676,033, filee Sep. 29, 2000 (6643R3).
Pending Application of Camden, Ser. No. 09/676,409, filed Sep. 29, 2000 (6643R4).
Pending Application of Camden, Ser. No. 09/676,032, filed Sep. 29, 2000 (6643R5).
Pending Application of Camden, Ser. No. 09/676,031, filed Sep. 29, 2000 (6643R6).
Pending Application of Camden, Ser. No. 09/676,030, filed Sep. 29, 2000 (6643R7).
Pending Application of Camden, Ser. No. 09/676,029, filed Sep. 29, 2000 (6643R8).
Pending Application of Camden, Ser. No. 09/676,408, filed Sep. 29, 2000 (6643R9).
Pending Application of Camden, Ser. No. 09/676,202, filed Sep. 29, 2000 (6643R10).
Pending Application of Camden Ser. No. 09/670,169, filed Sep. 26, 2000 (8250).
Pending Application of Camden, Ser. No. 09/670,168, filed Sep. 26, 2000 (8251).
Pending Application of Camden, Ser. No. 09/670,170, filed Sep. 26, 2000 (8252).
Pending Application of Camden, Ser. No. 09/670,166, filed Sep. 26, 2000 (8253).
Pending Application of Camden, Ser. No. 09/737,835, field Dec. 15, 2000 (5782C).
Pending Application of Camden, Ser. No. 09/748,651, filed Dec. 22, 2000 (5638D2CD).
Pendign Application of Camden, Ser. No. 09/748,652, filed Dec. 22, 2000 (5785D2RC).
Pending Application o Camden, Ser. No. Not Yet Correctly Assigned, field Feb. 23, 2001 (5702CRC).

* cited by examiner

METHODS OF TREATING VIRAL INFECTIONS WITH BENZIMIDAZOLES

This is a divisional application of copending application Ser. No. 09/264,942, filed Mar. 9, 1999 now U.S. Pat. No. 6,262,093, which is a continuation-in-part of application Ser. No. 08/927,550, filed Sep. 6, 1997, now U.S. Pat. No. 5,880,144, which is a divisional of application Ser. No. 08/771,193, filed Dec. 20, 1996, now U.S. Pat. No. 5,767,138, which is a divisional of application Ser. No. 08/420,914, filed Apr. 12, 1995, now abandoned. application Ser. No. 09/264,942, now U.S. Pat. No. 6,262,093 is also a continuation-in-part of application Ser. No. 09/081,384, filed May 19, 1998, now abandoned, and also a continuation-in-part of application Ser. No. 09/081,627, filed May 19, 1998, now abandoned.

TECHNICAL FIELD

This invention is a method of treating cancer, both carcinomas and sarcomas, and viral infections, in particular HIV through the administration of a pharmaceutical composition containing a benzimidazole derivative. The composition is also claimed.

BACKGROUND OF THE INVENTION

Cancers are the leading cause of death in animals and humans. The exact cause of cancer is not known, but links between certain activities such as smoking or exposure to carcinogens and the incidence of certain types of cancers and tumors has been shown by a number of researchers.

Many types of chemotherapeutic agents have been shown to be effective against cancers and tumor cells, but not all types of cancers and tumors respond to these agents. Unfortunately, many of these agents also destroy normal cells. The exact mechanism for the action of these chemotherapeutic agents are not always known.

Despite advances in the field of cancer treatment the leading therapies to date are surgery, radiation and chemotherapy. Chemotherapeutic approaches are said to fight cancers that are metastasized or ones that are particularly aggressive. Such cytocidal or cytostatic agents work best on cancers with large growth factors, i.e., ones whose cells are rapidly dividing. To date, hormones, in particular estrogen, progesterone and testosterone, and some antibiotics produced by a variety of microbes, alkylating agents, and antimetabolites form the bulk of therapies available to oncologists. Ideally cytotoxic agents that have specificity for cancer and tumor cells while not affecting normal cells would be extremely desirable. Unfortunately, none have been found and instead agents which target especially rapidly dividing cells (both tumor and normal) have been used.

The development of materials that would target tumor cells due to some unique specificity for them would be a breakthrough Alternatively, materials that were cytotoxic to tumor cells while exerting mild effects on normal cells would be desirable.

HIV and other viral infections are another leading cause of death. HIV is a disease in which a virus is replicated in the body which attacks the body's immune system. The HIV virus is not easily destroyed nor is there a good mechanism for keeping the host cells from replicating the virus. Herpes Simplex is another viral infection which is difficult, if not impossible, to cure. A method of treating these diseases and other viral infections is highly desirable. A material which would target the HIV virus and inhibit viral replication is highly desirable.

The benzimidazole derivatives used herein to treat cancer and/or viral infection have been used as fungicides and as antihelmetics.

SUMMARY OF THE INVENTION

A method of treating cancer, in particular, treating cancers in warm blooded animals and humans, comprising administering a therapeutically effective amount of a composition comprising a benzimidazole compound selected from the group consisting of:

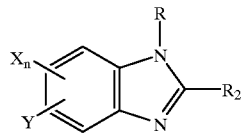

wherein X is hydrogen, halogen, alkyl of less than 7 carbon atoms or alkoxy of less than 7 carbon atoms; n is a positive integer of less than 4; Y is hydrogen, chlorine, nitro, methyl, ethyl or oxychloro; R is hydrogen, alkylaminocarbonyl wherein the alkyl group has from 3 to 6 carbon atoms, or an alkyl group of from 1 to 8 carbon atoms and $R_2$ is 4-thiazolyl, $NHCOOR_1$ wherein $R_1$ is aliphatic hydrocarbon of less than 7 carbon atoms, and preferably an alkyl group of less than 7 carbon atoms is claimed. Preferably the compositions contain:

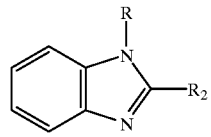

wherein R is an alkyl of 1 through 8 carbon atoms and $R_2$ is selected from the group consisting of 4-thiazolyl, $NHCOOR_1$, wherein $R_1$ is methyl, ethyl or isopropyl and the non-toxic, pharmaceutically acceptable acid salts with both organic and inorganic acids. The most preferred compounds are 2-(4-thiazolyl)benzimidazole, methyl-(butylcarbamoyl)-2-benzimidazolecarbamate and 2-methoxycarbonylamino-benzimidazole and those wherein Y is chloro.

In the present invention it has been discovered that the compounds described above are useful for the inhibition of HIV and the treatment of HIV infection and similar retrovirus infections. The present invention also provides methods for the treatment of HIV infection comprising administering to a host infected with HIV a pharmaceutically or therapeutically effective or acceptable amount of a compound as described above, particularly those wherein R is 4-thiazolyl.

The present invention also provides a pharmaceutical composition comprising a pharmaceutically acceptable carrier and a therapeutically effective amount of a compound as described above.

These compositions have been discovered to inhibit the growth of cancer or other tumors in humans or animals and to induce apoptosis of cancer cells by administration of a therapeutically effective amount of the composition, preferably by administering a benzimidazole compound to the site of the cancer.

More specifically, this invention provides an anticancer composition comprising a pharmaceutical carrier and a benzimidazole derivative as defined herein along with a method for treating such cancers. These compositions can induce apoptosis in cancer cells.

These compositions are also effective against viruses and are used to treat viral infections and this invention provides a method of treating viral infections such as herpes, hepatitis, influenza and rhinoviruses.

DETAILED DESCRIPTION OF THE INVENTION

A. DEFINITIONS

As used herein, a "pharmaceutically acceptable" component is one that is suitable for use with humans and/or animals without undue adverse side effects (such as toxicity, irritation, and allergic response) commensurate with a reasonable benefit/risk ratio.

As used herein, the term "safe and effective amount" refers to the quantity of a component which is sufficient to yield a desired therapeutic response without undue adverse side effects (such as toxicity, irritation, or allergic response) commensurate with a reasonable benefit/risk ratio when used in the manner of this invention. By "therapeutically effective amount" is meant an amount of a compound of the present invention effective to yield the desired therapeutic response. For example to inhibit HIV infection or treat the symptoms of infection in a host or an amount effective to delay the growth of or to cause a cancer, either a sarcoma or lymphoma, to shrink. The specific safe and effective amount or therapeutically effective amount will, vary with such factors as the particular condition being treated, the physical condition of the patient, the type of mammal being treated, the duration of the treatment, the nature of concurrent therapy (if any), and the specific formulations employed and the structure of the compounds or its derivatives.

As used herein, a "pharmaceutical salts" is salt of the benzimidazole derivatives which are modified by making acid or base salts of the compounds. Examples of pharmaceutically acceptable salts include, but are not limited to, mineral or organic acid salts of basic residues such as amines; alkali or organic salts of acidic residues such as carboxylic acids. Preferably the salts are made using an organic or inorganic acid. These preferred acid salts are chlorides, bromides, sulfates, nitrates, phosphates, sulfonates, formates, tartrates, maleates, malates, citrates, benzoates, salicylates, ascorbates, and the like.

As used herein, a "pharmaceutical carrier" is a pharmaceutically acceptable solvent, suspending agent or vehicle for delivering the benzimidazole derivatives to the animal or human. The carrier may be liquid or solid and is selected with the planned manner of administration in mind.

As used herein, "cancer" refers to all types of cancer or neoplasm or malignant tumors found in mammals, including carcinomas and sarcomas. Examples of cancer are cancer of the brain, breast, cervix, colon, head & neck, kidney, lung, nonsmall cell lung, melanoma, mesothelioma, ovary, sarcoma, stomach, uterus and Medulloblastoma.

As used herein, the "benzimidazole derivatives" are the benzimidazoles, and their salts and also their prodrugs. The exact benzimidazoles are described in detail below. The preferred materials are the products sold under the names "Thiabendazole®", "Benomyl®" and "Carbendazim®" by BASF and Hoechst, DuPont and MSD-AgVet.

As used herein "viruses" includes viruses which infect animals or mammals, including humans. Viruses includes retorviruses, IRV, influenza, polio viruses, herpes, herpes simplex, rhinoviruses, hepatitis, and the like.

B. THE BENZIMIDAZOLE DERIVATIVES

The benzimidazole derivatives which are known for their antifungal activities. They are systemic fungicides used to prevent and eradicate fungi. The compounds have the following structure:

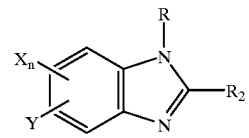

wherein X is hydrogen, halogen, alkyl of less than 7 carbon atoms or alkoxy of less than 7 carbon atoms; n is a positive integer of less than 4; Y is hydrogen, chlorine, nitro, methyl, ethyl, or oxychloro; R is hydrogen, alkylaminocarbonyl wherein the alkyl group has from 3 to 6 carbon atoms or an alkyl group having from 1 to 8 carbons, and $R_2$ is 4-thiazolyl, $NHCOOR_1$ wherein $R_1$ is aliphatic hydrocarbon of less than 7 carbon atoms, and preferably and alkyl group of less than 7 carbon atoms. Preferably the compositions are:

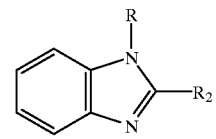

wherein R is an alkyl of 1 through 8 carbon atoms and $R_2$ is selected from the group consisting of 4-thiazolyl, $NHCOOR_1$, wherein $R_1$ is methyl, ethyl or isopropyl and the non-toxic, pharmaceutically acceptable acid salts with both organic and inorganic acids.

The most preferred compounds are 2-(4-thiazolyl) benzimidazole, methyl-(butylcarbamoyl)-2-benzimidazolecarbamate and 2-methoxycarbonylamino-benzimidazole and the compounds wherein Y is chloro and X is hydrogen.

The benzimidazole compounds also include prodrugs. "Prodrugs" are considered to be any covalently bonded carriers which release the active parent drug according to the formula of the benzimidazole derivatives described above in vivo when such prodrug is administered to a mammalian subject. Prodrugs of the benzimidazole compounds are prepared by modifying functional groups present in the compounds in such a way that the modifications are cleaved, either in routine manipulation or in vivo, to the parent compounds. Prodrugs include compounds wherein hydroxy, amine, or sullhydryl groups are bonded to any group that, when administered to a mammalian subject, cleaves to form a free hydroxyl, amino, or sullhydryl group, respectively. Examples of prodrugs include, but are not limited to, acetate, formate, or benzoate derivatives of alcohol and amine functional groups in the benzimidazole derivatives; phosphate esters, dimethylglycine esters, aminoalkylbenzyl esters, aminoalkyl esters and carboxyalkyl esters of alcohol and phenol functional groups in the benzimidazole derivatives; and the like.

The pharmaceutically acceptable salts of the benzimidazole derivatives include the conventional non-toxic salts or the quaternary ammonium salts of the benzimidazole derivatives formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 1-acetoxybenzoic, fumaric, toluenesulfonic, methanesulfonic, ethane disulfonic, oxalic, isethionic, and the like.

The pharmaceutically acceptable salts of the present invention are synthesized from the benzimidazole derivatives which contain a basic or acidic moiety by conventional chemical methods. Generally, such salts are prepared by reacting the free acid or base forms of these compounds with a stoichiometric amount of the appropriate base or acid in water or in an organic solvent, or in a mixture of the two, generally, nonaqueous media like ether, ethyl acetate, ethanol, isopropanol, or acetonitrile are preferred. Lists of suitable salts are found in Remington's Pharmaceutical Sciences, 17th ed., Mack Publishing Company, Easton, Pa., 1985, p. 1418, the disclosure of which is hereby incorporated by reference. The disclosures of all of the references cited herein are hereby incorporated herein by reference in their entirety.

SYNTHESIS

The benzimidazole derivatives are prepared in a number of ways well known to one skilled in the art of organic synthesis. The benzimidazole derivatives are synthesized using the methods described below, together with synthetic methods known in the art of synthetic organic chemistry, or variations thereon as appreciated by those skilled in the art. Preferred methods include but are not limited to those methods described below. Each of the references cited below are hereby incorporated herein by reference.

These compounds are prepared according to the method described in U.S. Pat. No. 3,738,995 issued to Adams et al, Jun. 12, 1973. The thiazolyl derivatives are prepared according to the method described in Brown et al., *J. Am. Chem. Soc.* 83, 1764 (1961) and Grenda et al., *J. Org. Chem.* 30, 259 (1965).

C. DOSAGE AND DOSAGE DELIVERY FORMS

The type of compound and the carrier and the amount will vary widely depending on the species of the warm blooded animal or human, body weight, and tumor being treated. The dosage administered will vary depending upon known factors, such as the pharmacodynamic characteristics of the particular agent and its mode and route of administration; the age, health and weight of the recipient; the nature and extent of the symptoms; the kind of concurrent treatment; the frequency of treatment; and the effect desired.

The benzimidazole is preferably micronized or powdered so that it is more easily dispersed and solubilized by the body. Processes for grinding or pulverizing drugs are well known in the art. For example, a hammer mil or similar milling device are used. The preferred particle size is less than about 100μ and preferably less than 50μ.

The dosage administered will vary depending upon known factors such as the pharmacodynamic characteristics of the particular active ingredient, and its mode and route of administration; age, sex, health, metabolic rate, absorptive efficiency and/or weight of the recipient; nature and extent of symptoms; kind of concurrent treatment, frequency of treatment; and the effect desired.

A "tumor growth inhibiting amount" of the benzimidazole derivatives is that amount which is effective to inhibit or slow the growth of a tumor.

Dosage forms (compositions) suitable for internal administration contain from about 1.0 milligram to about 5000 milligrams of active ingredient per unit. In these pharmaceutical compositions, the active ingredient will ordinarily be present in an amount of about 0.5–95% by weight based on the total weight of the composition. Based on the body weight of the patent, the dosage may be administered in one or more doses several times per day or per week. Multiple dosage units may be required to achieve a therapeutically effective amount. For example, if the dosage form is 1000 mg, and the patient weighs 40 kg, one pill will provide a dose of 25 mg per kg for that patient. It will provide a dose of only 12.5 mg/kg for a 80 kg patient.

The compounds have shown dose responsiveness in vivo against viruses and cancers in mice at 500 mg/kg, 2500 mg/kg, 3500 mg/kg, 4000 mg/kg, 5000 mg/kg and 6000 mg/kg. Generally a dosage effective in mice translates to about 1/12 of the dosage required in humans. By way of general guidance, for humans a dosage of as little as about 30 milligrams (mg) per kilogram (kg) of body weight and up to about 10000 mg per kg of body weight is suitable. Preferably from 50 mg/kg to about 5000 mg/kg of body weight is used. Most preferably the doses are between 100 mg/kg to about 3000 mg/kg of body weight. However, a dosage of between about 2 milligrams (mg) per kilogram (kg) of body weight to about 400 mg per kg of body weight is also suitable for some indications.

Intravenously, the most preferred doses may range from about 1 to about 1000 mg/kg/minute during a constant rate infusion. Benzimidazole derivatives may be administered in a single daily dose, or the total daily dosage may be administered in divided doses of two, three, or four times daily. The benzimidazole derivatives are given in one or more doses on a daily basis or from one to three times a week.

The benzimidazole derivatives may also be administered in intranasal form via topical use of suitable intranasal vehicles, or via transdermal routes, using those forms of transdermal slim patches well known to those of ordinary skill in that art. To be administered in the form of a transdermal delivery system, the dosage administration will, of course, be continuous rather than intermittant throughout the dosage regimen.

Generally, the dosage in man is lower than for small warm blooded mammals such as mice. A dosage unit may comprise a single compound or mixtures thereof with other compounds or other cancer inhibiting compounds or tumor growth inhibiting compounds or antiviral compounds. The dosage unit can also comprise diluents, extenders, carriers and the like. The unit may be in solid or gel form such as pills, tablets, capsules and the like or in liquid form suitable for oral, rectal, topical, intravenous injection or parenteral administration or injection into or around the tumor.

The benzimidazole derivatives are typically mixed with a pharmaceutically acceptable carrier. This carrier can be a solid or liquid and the type is generally chosen based on the type of administration being used. The active agent can be coadministered in the form of a tablet or capsule, as an agglomerated powder or in a liquid form. Examples of suitable solid carriers include lactose, sucrose, gelatin and agar. Capsule or tablets are easily formulated and can be made easy to swallow or chew; other solid forms include granules, and bulk powders. Tablets may contain suitable binders, lubricants, diluents, disintegrating agents, coloring agents, flavoring agents, flowinducing agents, and melting agents. Examples of suitable liquid dosage forms include solutions or suspensions in water, pharmaceutically acceptable fats and oils, alcohols or other organic solvents, including esters, emulsions, syrups or elixirs, suspensions, solutions and/or suspensions reconstituted from non-effervescent granules and effervescent preparations reconstituted from effervescent granules. Such liquid dosage forms may contain, for example, suitable solvents, preservatives, emulsifying agents, suspending agents, diluents, sweeteners, thickeners, and melting agents. Oral dosage forms optionally contain flavorants and coloring agents. Parenteral and intravenous forms would also include minerals and other materials to make them compatible with the type of injection or delivery system chosen.

D. EXAMPLES OF FORMULATION

The benzimidazole derivatives of this invention are administered as treatment for cancer and viral infections, including retroviral, by any means that produces contact of the active agent with the agent's site of action in the body. The antitumor compounds (active ingredients) of this invention are administered to inhibit tumors by any means that produces contact of the active ingredient with the agent's site of action in the body of a mammal. They can be administered by any conventional means available for use in conjunction with pharmaceuticals, either as individual therapeutic agents or in a combination of therapeutic agents. They can be administered alone, but generally are administered with a pharmaceutical carrier selected on the basis of the chosen route of administration and standard pharmaceutical practice.

The benzimidazole derivatives are administered in oral dosage forms as tablets, capsules (each of which includes sustained release or timed release formulations), pills, powders, granules, elixirs, tinctures, suspensions, syrups, and emulsions. The benzimidazole derivatives may also be administered in intravenous (bolus or infusion), intraperitoneal, subcutaneous, or intramuscular form, all using dosage forms well known to those of ordinary skill in the pharmaceutical arts.

In the methods of the present invention, the compounds herein described in detail can form the active ingredient, and are typically administered in admixture with suitable pharmaceutical diluents, excipients, or carriers (collectively referred to herein as a pharmaceutically acceptable carrier or carrier materials) suitably selected with respect to the intended form of administration, that is, oral tablets, capsules, elixirs, syrups and the like, and consistent with conventional pharmaceutical practices.

For instance, for oral administration in the dosage unit form of a tablet or capsule, the active drug component can be combined with an oral, non-toxic, pharmaceutically acceptable, inert carrier such as lactose, starch, sucrose, glucose, methyl cellulose, magnesium stearate, dicalcium phosphate, calcium sulfate, mannitol, sorbitol and the like.

For oral administration in liquid dosage form, the oral drug components are combined with any oral, non-toxic, pharmaceutically acceptable inert carrier such as ethanol, glycerol, water, and the like. Moreover, when desired or necessary, suitable binders, lubricants, disintegrating agents, and coloring agents can also be incorporated into the mixture. Suitable binders include starch, gelatin, natural sugars such as glucose or betalactose, corn sweeteners, natural and synthetic gums such as acacia, tragacanth, or sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. Disintegrators include, without limitation, starch, methyl cellulose, agar, bentonite, xanthan gum, and the like.

The benzimidazole derivatives can also be administered in the form of liposome delivery systems, such as small unilamallar vesicles, large unilamallar vesicles, and multilamellar vesicles. Liposomes can be formed from a variety of phospholipids, such as cholesterol, stearylamine, or phosphatidylcholines.

Benzimidazole derivatives may also be coupled with soluble polymers as targetable drug carriers. Such polymers can include polyvinylpyrrolidone, pyran copolymer, polyhydroxylpropylmethacrylamime-dephenol, polyhydroxyethylaspartamimedephenol, or polyethyleneoxidepolylysine substituted with paimitoyl residues. Furthermore, the compounds of the present invention may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacylates, and crosslinked or amphipathic block copolymers of hydrogels.

The active ingredient can be administered orally in solid dosage forms, such as capsules, tablets, and powders, or in liquid dosage forms, such as elixirs, syrups, and suspensions. It can also be administered parentally, in sterile liquid dosage forms.

Gelatin capsules may contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance. In general, water, a suitable oil, saline, aqueous dextrose (glucose), and related sugar solutions and glycols such as propylene glycol or polyethylene glycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabbing agents. Also used are citric acid and its salts and sodium EDTA. In addition, parenteral solutions can contain preservatives, such as benzalkonium chloride, methyl- or propyl-paraben, and chlorobutanol. Suitable pharmaceutical carriers are described in Remington's Pharmaceutical Sciences, Mack Publishing Company, a standard reference text in this field.

Useful pharmaceutical dosage forms for administration of the compounds of this invention are illustrated as follows:

Capsules

A large number of unit capsules are prepared by filling standard two-piece hard gelatin capsules each with 100 to 500 milligrams of powdered active ingredient, 5–150 milligrams of lactose, 5–50 milligrams of cellulose, and 6 milligrams magnesium stearate.

Soft Gelatin Capsules

A mixture of active ingredient in a digestible oil such as soybean oil, cottonseed oil or olive oil is prepared and injected by means of a positive displacement pump into gelatin to form soft gelatin capsules containing 100–500 milligrams of the active ingredient. The capsules are washed and dried.

Tablets

A large number of tablets are prepared by conventional procedures so that the dosage unit was 100–500 milligrams of active ingredient, 0.2 milligrams of colloidal silicon dioxide, 5 milligrams of magnesium stearate, 50–275 milligrams of microcrystalline cellulose, 11 milligrams of starch and 98.8 milligrams of lactose. Appropriate coatings may be applied to increase palatability or delay absorption.

Injectable

A parenteral composition suitable for administration by injection is prepared by stirring 1.5% by weight of active ingredient in 10% by volume propylene glycol and water. The solution is made isotonic with sodium chloride and sterilized.

Suspension

An aqueous suspension is prepared for oral administration so that each 5 ml contain 100 mg of finely divided active ingredient, 200 mg of sodium carboxymethyl cellulose, 5 mg of sodium benzoate, 1.0 g of sorbitol solution, U.S.P., and 0.025 ml of vanillin.

The present invention also includes pharmaceutical kits useful, for example, for the treatment of HIV infection, which comprise one or more containers containing a pharmaceutical composition comprising a therapeutically effective amount of a benzimidazole derivative. Such kits may further include, if desired, one or more of various conventional pharmaceutical kit components, such as, for example, containers with one or more pharmaceutically acceptable carriers, additional containers, etc., as will be readily apparent to those skilled in the art. Printed instructions, either as inserts or as labels, indicating quantities of the components to be administered, guidelines for administration, and/or guidelines for mixing the components, may also be included in the kit. In the present disclosure it should be understood that the specified materials and conditions are important in practicing the invention but that unspecified materials and conditions are not excluded so long as they do not prevent the benefits of the invention from being realized.

The following examples are illustrative and are not meant to be limiting to the invention.

Colon, Breast and Lung Tumor Cells Test

The following cell culture tests were performed to test the toxicity of the benzimidazole compounds on colon, breast and lung human tumor cells. The viability of the cells were tested by looking at MTT (3-[4,5dimethylthiazol2-yl] -2,5-diphenyltetrazolium bromide) reduction. MTT assay is a well known measure of cell viability.

The colon tumor cells (HT29 from American Type Culture Collection (ATCC) and the breast cells (MX1 from cell lines from ATCC) were cultured in Eagle's Miminal Essential Medium with 10% fetal bovine serum. The lung tumor cells (A549 from ATCC cell lines) were cultured in Ham's F12 medium with 10% fetal bovine serum.

The tumor cells were passaged and seeded into culture flasks at the desired cell densities. The culture medium was decanted and the cell sheets were washed twice with phosphate buffered saline (PBS). The cells were trypsinized and triturated prior to seeding the flasks. Unless otherwise indicated the cultures were incubated at 37±1° C. in a humidified atmosphere of 5±1% carbon dioxide in air. The cultures were incubated until they were 50–80% confluent.

The cells were subcultured when the flasks were subconfluent. The medium was aspirated from the flasks and the cell sheets rinsed twice with PBS. Next, the Trypsin Solution was added to each flask to cover the cell sheet. The Trypsin Solution was removed after 30–60 seconds and the flasks were incubated at room temperature for two to six minutes. When 90% of the cells became dislodged, growth medium was added. The cells were removed by trituration and transferred to a sterile centrifuge tube. The concentration of cells in the suspension was determined, and an appropriate dilution was made to obtain a density of 5000 cells/ml. The cells were subcultured into the designated wells of the 96-well bioassay plates (200 microliter cell suspension per well). PBS was added to all the remaining wells to maintain humidity. The plates were then incubated overnight before test article treatment.

Each dose of test article was tested by treating quadruplicate wells of cultures with 100 microliter of each dilution. Those wells designated as solvent controls received an additional 100 microliter of methanol control; negative controls wells received an additional 100 microliters of treatment medium. PBS was added to the remaining wells not treated with test article or medium. The plates were then incubated for approximately 5 days.

At the end of the 5 day incubation, each dose group was examined microscopically to assess toxicity. A 0.5 mg/ml dilution of MTT was made in treatment medium, and the dilution was filtered through a 0,.45 micrometer filter to remove undissolved crystals. The medium was decanted from the wells of the bioassy plates. Immediately thereafter, 2000 microliter of the filtered MTT solution was added to all test wells except for the two untreated blank test wells. The two blank wells received 200 microliters of treatment medium. The plates were returned to the incubator for about 3 hours. After incubation, the MTT containing medium was decanted. Excess medium was added to each well and the plates were shaken at room temperature for about 2 hours.

The absorbance at 550 nm ($OD_{550}$) of each well was measured with a Molecular Devices (Menlo Park, Calif.) VMax plate reader.

The mean $OD_{550}$ of the solvent control wells and that of each test article dilution, and that of each of the blank wells and the positive control were calculated. The mean $OD_{550}$ of the blank wells was subtracted from the mean of the solvent control wells, and test article wells, respectively to give the corresponding mean $OD_{550}$.

$$\% \text{ of Control} = \frac{\text{corrected mean } OD_{550} \text{ of Test Article Dilution}}{\text{corrected mean of } OD_{550} \text{ of Solvent Control}} \times 100$$

Dose response curves were prepared as semilog plots with % of control on the ordinate (linear) and the test article concentration on the abscissa (logarithmic). The $EC_{50}$ was interpolated from the plots for each test article.

For the test articles administered in methanol, separate responses were prepared to correct for the methanol data.

Adriamycin was used as a positive control. In all cases, it was more toxic than any of the test materials by one or two logs. Adriamycin is one of the more potent agents in current use and one with significant side effects. The peak plasma concentration of other, quite effective chemotherapeutic agents may be 10 to 50 times higher than that of Adriamycin.

The $EC_{50}$ is the concentration at which one half of the cells are killed.

TABLE 1

| | EC-50 Result (ppm) | | | | | |
|---|---|---|---|---|---|---|
| Test Material | HT29 | HT29 | MX1 | MX1 | A549 | A549 |
| Adriamycin | 0.03 | 0.006 | 0.02 | 0.001 | 0.03 | 0.009 |
| benomyl | 0.742 | 0.747 | 1.42 | 2.42 | 0.980 | 1.02 |
| carbendazim | 0.621 | 0.662 | 0.829 | 0.856 | 0.856 | 0.836 |

In normal healthy cells, the following results were obtained. As is evident, the benomyl and carbendazim were much less toxic to normal healthy cells than adriamycin.

TABLE 2

| | EC-50 | | | | | |
|---|---|---|---|---|---|---|
| Test Material | Broncheal Cells | | Kerotinoyle Cells | | Fibroblasts | |
| Benomyl | 0.728 | 0.682 | 3.26 | 2.4 | 3.24 | 2.81 |
| Carbendazim | 0.320 | 0.506 | 0.752 | 0.822 | 1.52 | 1.42 |
| Adriamycin | 0.015 | 0.0020 | 0.0035 | 0.0093 | 0.065 | 0.10 |

In a related study using lung tumor cells (A-549) breast tumor cells (MCF-7) and colon tumor cells (HT-29), thiabeadazole effectively killed these cells. Table 3 summarizes the results

TABLE 3

| | Optical Density | | |
|---|---|---|---|
| Concentration (ppm) | A-549 | MCF-7 | HT-29 |
| 0-Control | 0.600 | 0.245 | 0.398 |
| 173 | 0.007 | 0.007 | 0.005 |
| 35 | 0.411 | 0.025 | 0.011 |
| 17.3 | 0.851 | 0.258 | 0.204 |
| 3.46 | 1.12 | 0.466 | 0.713 |
| 0.87 | 1.32 | 0.507 | 0.852 |

These experiments show that these compositions are effective in killing tumor cells of the breast, colon and lung type.

Carbendazim has shown broadscale efficacy against multiple cancer types both in vitro and in vivo. The cancers tested include colon, lung, breast, prostate, pancreatic, leukemia, melanoma, neuroblastoma, ovarian, neck and head, and brain. Also multiple cell lines were tested in almost instances.

The initial efficacy is comparable to existing best available drugs. But with carbendazir, the tumors do not recur or reappear as happens with Cytoxan and Taxol, which otherwise are quite good against breast cancer. Similarly, pancreatic cancer does not appear to come back as often happens with Gemcitabine treatment.

Carbendazim is particularly good in mouse melanoma in mice, which many people believe is the best predictive model for efficacy in humans. It has shown outstanding broad and good results in the human tissue cloning test. This is an in vitro test on conventionally treated and recently excised human tumors.

Carbendazim is equally effective against p53 deficient/defective cell lines, unlike most existing drugs. It appears that carbendazim induces apoptosis in cancer cells at sublethal concentrations to normal cells.

Other benefits of carbendazim are:
Its oral $LD_{50}$ in mice is quite high (11,000 mg/kg), a low overall toxicity unlike most cancer drugs. For perspective the $LD_{50}$ of table salt is 3750 mg/kg.

It is effective in cancers that form tumors and those that do not, e.g. both carcinomas and sarcomas.

The results of these studies are provided in more detail below.

Mechanism of Action Studies

Some of the pharmacological effects of carbendazim were demonstrated by An studying its ability to induce apoptosis in cancer cells, studying its effect on p53-abnormal cell lines and determining during which cellular life cycle phase carbendazim exerts its effects.

Apoptosis Study:

Apoptosis is a specific type of cell death which differs from necrosis and is characterized by specific morphological, biochemical and micelular cell changes. Abnormalities in p53 expression are generally linked with the prevention of apoptosis and p53 abnormalities are common in human tumors which are resistant to conventional cytotoxic agents.

Summary of test results: The extent of apoptosis is measured in human tumor cell lines after treatment for 1, 2, 3 and 4 days with carbendazim. At each of these time points, the cells are harvested and assayed using the terminal deoxynucleotidyl transferase (TdT) assays. Both microscopy and flow cytometry were used for the TdT assay.

In MCF7, HT29, B16 and SK-MES cell lines, there was a concentration dependent effect on cell growth. In most cases at concentrations of carbendazim greater than 1 $\mu$g/ml the growth rate was significantly slower than in the untreated samples. After completion of the studies on the MCF7 and HT29 cell lines, it was evident that the 0.1 $\mu$g/ml concentration had little effect on either apoptosis or cell growth. Therefore subsequent assays were with 5 $\mu$g/ml instead of 0.1 $\mu$g/ml.

The growth of MCF7 (breast cancer) cells was not significantly affected by carbendazim below 10 $\mu$g/ml as shown by either method. However, at 10 $\mu$g/ml the increase in apoptosis was evident at days 3 and 4. The increase in apoptosis was low, less than 10% at the high concentration. After normalization for the cell growth, carbendazim at 10 $\mu$g/ml had an effect at day 4.

The growth of HT29 (colon) cancer cells was not largely slowed down by carbendazim below 10 $\mu$g/ml. Concentrationdependent increase in apoptosis was observed at days 3 and 4, reaching >25% apoptosis in the presence of 10 $\mu$g/ml carbendazim. After normalization for the cell growth rates, the concentration-response effect was seen at day 4.

At all concentrations, carbendazim affected the growth rates in B16 murine melanoma cell line. Some concentration dependent effects on apoptosis were seen at days 14 by TdT microscopy and days 2–4 by flow cytometry. The concentration effects at days 1–4 were much more evident after normalization of the apoptosis for the growth rates.

The growth of SK-MES cells was slowed done by all concentrations of carbendazim past day 1. The percent of apoptosis showed a concentration-response effect at days 1–4 by microscopic TdT assay and by flow cytometry at days 3 and 4. A normalized graph showed a concentration response effect of the compound on apoptosis at all days.

Conclusion: At concentrations less than 10 $\mu$g/ml, the greatest response to carbendazim was seen in the SK-MES lines (lung), followed by B16 (murine melanoma), HT29 (colon), and MCF7 (breast) cells. The HT29, SK-MES and B16 cell lines express abnormal p53. Accordingly carbendazim can induce apoptosis in p53 abnormal cell lines.

Selectivity in Killing p53 Abnormal Cell Lines

Carbendazim provides in vivo activity against HT29 tumor cells which express abnormal p53.

Summary of lest results: Pairs of tumors of the same type were chosen, one expressing normal p53 and the other abnormal p53. Breast lines used were MCF7 for the normal p53, V4B, a MCF7 cells transformed with an empty vector, and VM4K, an MCF7 cells transfected with a vector encoding abnormal p53. In the colorectal cancer model HCT116 with a normal p53 was used and DLD-1 was used as the abnormal p53 cell line. The tumor cells were grown the presence and absence of carbendazim for 7 days. Cell growth rates were determined in each group by counting the cell numbers daily using a Coulter counter.

In the breast model at day 7, using 1 µg/ml of carbendazim, cell counts in all three cell lines were between 50% and 60% of the control. At concentrations of 5 and 10 µg/ml the MCF7 cell counts were 45% and 36% of the control. The V4B and VM4K cell lines were less than 10% of the respective controls. The data from the VM4K cell line would also indicate the carbendazim is again selectively killing the p53 abnormal cells, however, there was also a marked decrease in the cell numbers in the V4B line carrying only the empty vector. In light of the controversy regarding the p53 status in MCF7 cells, which some researchers claim to express abnormal p53, these differences may be more difficult to interpret.

At day 7 in the colorectal model, at 1 µg/ml concentration carbendazim cell counts in the DLD1 line (abnormal p53) were only 34% of the control. The HCT 116 cell line, (normal p53) showed cell counts that were 78% of the control suggesting that carbendazim may selectively kill p53 abnormal cells. At carbendazim concentrations of 5 and 10 µg/ml, cell counts were less than 10% of the control in both the DLD-1 and HCT116 lines indicating that at the larger concentration, the drug was equally toxic to cell lines containing abnormal and normal p53.

Conclusion: At higher concentrations, 5 and 10 µg/m the drug was equally toxic to cell lines containing abnormal p53 and normal p53 in both colon and breast cancers.

In Vitro Studies of Carbendazim on Cancer Cell Lines

A dose response effect of carbendazim in a human tumor cloning forming units study (HTCU) is summarized below. This is an in vitro test of treatments on conventionally treated, then recently excised human tumors. It is an important study because carbendazim is showing effectiveness against cell lines which have survived conventional treatment and which themselves have not had undergone too many passages (due to recent excision). This is significant since long living cell lines undergo changes (passages), some of which may affect their resistance to some drugs, and hemotherapeutic agent resistant cells can be formed. The data show the activity as the tumors tested that had ≧50% survival (a high number is desirable).

In Vitro Human Tumor Colony Forming Units Test

Solid tumors removed by patients are minced into 2 to 5 mm fragments and immediately placed in McCoy's Medium 5A plus 10% heat inactivated newborn calf serum plus 1% penicininstreptomycin. Within 4 hours, these solid tumors are mechanically disassociated with scissors, forced through No. 100 stainless steel mesh, through 25 gauge needles, and then washed with McCoy's medium as described above. Ascitic, pleural, pericardial fluids and bone marrow are obtained by standard techniques. The fluid or marrow is placed in sterile containers containing 10 units of preservative free heparin per ml. of malignant fluid or marrow. After centrifugation at 150×g for 10 minutes, the cells are harvested and washed with McCoy's medium plus 10% heat inactivated calf serum. The viability of cell suspensions is determined on a hemocytometer with trypan blue.

Cells to be cloned are suspended in 0.3% agar in enriched CMRL1066 supplemented with 15% heat inactivated horse serum, penicillin (100 units/ml), streptomycin (2 mg/ml), glutamine (2 mM), insulin (3 units/ml), asparagine (0.6 mg/ml), and HEPES buffer (2 mM). For the continuous exposure test each compound is added to the above mixture. Cells are placed in 35 mm petri dishes in a top layer of agar over an underlayer of agar to prevent growth of fibroblasts. Three plates are prepared for each data point. The plates are placed in a 37° C. incubator, and are removed on day 14 for counting of the number of colonies in each plate. The number of colonies (defined as 50 cells) formed in the 3 compound treated plates is compared to the number of colonies formed in the 3 control plates, and the percent colonies surviving at the concentration of compound can be estimated. Three positive control plates are used to determine survival rate. Orthosodium vanadate at 200 µg/ml is used as the positive control. If there is <30% colonies in the positive control when compared to the untreated control, the test is evaluated.

Activity of Carbendazim Against Human Tumor Colony Forming Units

| Tumor Type | 1 Hour Exposure Concentration - µg/ml | | | 1 Hour Exposure Concentration - µg/ml | | | |
|---|---|---|---|---|---|---|---|
| | 0.5 | 5.0 | 50 | 0.5 | 5.0 | 10 | 50 |
| Brain | — | — | — | 0/2 | 0/2 | — | 2/2 |
| Breast | 0/1 | 0/1 | 0/1 | 0/3 | 0/4 | 0/1 | 2/3 |
| Cervix | — | — | — | 0/1 | 0/1 | — | 1/1 |
| Colon | 0/1 | 0/1 | 0/1 | 0/5 | 1/5 | — | 2/5 |
| Head & Neck | 0/1 | 0/1 | 0/1 | 0/1 | 0/1 | — | 1/1 |
| Kidney | 0/1 | 0/1 | 0/1 | 0/2 | 0/2 | — | 1/2 |
| Lung, non-small cell | 0/1 | 0/1 | 0/1 | 0/6 | 2/6 | 0/1 | 2/5 |
| Melanoma | 0/2 | 0/2 | 1/2 | 0/3 | 1/3 | — | 2/3 |
| Mesothelioma | — | — | — | 0/1 | 0/1 | 0/1 | — |
| Ovary | 0/3 | 0/3 | 0/3 | 0/1 | 2/13 | — | 10/13 |
| Sarcoma | 0/1 | 0/1 | 1/1 | 0/1 | 0/1 | — | 1/1 |
| Stomach | — | — | — | 0/1 | 0/1 | — | 1/1 |
| Uterus | — | — | — | 0/3 | 0/3 | — | 2/3 |
| Unknown Primary | — | — | — | 0/1 | 0/1 | — | 0/1 |
| | 0/11 | 0/11 | 2/11 | 0/4 | 6/44 | 0/3 | 27/41 |
| | 0% | 0% | 18% | 0% | 14% | 0% | 66% |

(4-thiazolyl)-1-H-benzimidazole shows efficacy in the Human Tumor Colony Forming Units test described above when tested using continuous exposure of the cells to the (4-thiazolyl)-1-H-benzimidazole.

The following table summarizes these results showing positive results on a number of cancer types:

| Compound | 1 Hour Exposure Concentration - µg/ml | | | Continuous Exposure Concentration - µg/ml | | |
|---|---|---|---|---|---|---|
| | 0.5 | 5.0 | 50.0 | 0.5 | 5.0 | 50.0 |
| 2-(methoxycarbonyl-amino)benzimidazole | 0/1 | 0/1 | 0/1 | 0/14 | 3/14 | 5/14 |
| (4-thiazolyl)-1H-benzimidazole | 0/3 | 0/3 | 0/3 | 1/10 | 2/10 | 7/10 |

In Vivo Studies of Carbendazim on Cancer Cell Lines

The dose response effect of carbendazim in mice infected with various cancer types was studied in standard screening tests.

The results of these studies conducted to study the dosage response of carbendazim on various cancer types are summarized below. These results are representative of a number of tests in which a known chemotherapeutic agent is used as the control so that the efficacy of the carbendazim can be compared to it. Efficacy of carbendazim has been shown in the following cancers:

In a Prostate cancer model doses of 4000, 5000 and 6000 (mg/kg given once weekly) were as effective as Mitoxantrone at 70 days. It was better than Cytoxan at these doses of 4000, 5000 and 6000 (mg/kg given twice weekly) through 40 days. The tables show tumor weight in mg for each dose. The carbendazim was given once a week (p.o) and the Mitoxantrone was given by i.v. (q.d.×5).

| dose | day 1 | day 5 | day 9 | day 12 | day 16 | day 19 |
|---|---|---|---|---|---|---|
| peanut oil control | 61.6 | 88.9 | 146.8 | 184.9 | 278.1 | 305.8 |
| 6000 mg/kg carbendazim | 62.1 | 92.2 | 140.4 | 162 | 226.5 | 275.99 |
| 5000 mg/kg carbendazim | 63.1 | 100.1 | 116.8 | 138.3 | 280.4 | 246.9 |
| 4000 mg/kg carbendazim | 63.1 | 97.5 | 159 | 192.7 | 282.1 | 311.6 |
| Mitoxantrone 1.5 mg/kg | 61.9 | 91.5 | 120.4 | 150.9 | 169.7 | 187.1 |

| dose | day 23 | day 26 | day 30 | day 33 | day 37 | day 40 |
|---|---|---|---|---|---|---|
| peanut oil control | 385.6 | 592.4 | 518 | 625.2 | 537.6 | 594 |
| 6000 mg/kg carbendazim | 301.9 | 400.9 | 416.6 | 447.3 | 546.3 | 514.4 |
| 5000 mg/kg carbendazim | 281.3 | 374.6 | 370.6 | 428.6 | 406.4 | 391.6 |
| 4000 mg/kg carbendazim | 316.6 | 368.1 | 351.3 | 410.7 | 506.8 | 484.9 |
| Mitoxantrone 1.5 mg/kg | 208.5 | 248 | 247.3 | 296.9 | 363 | 465 |

| dose | day 44 | day 47 | day 51 | day 53 | day 59 | day 61 |
|---|---|---|---|---|---|---|
| peanut oil control | 714.1 | 777.4 | 665.7 | 764.8 | 981.3 | 936 |
| 6000 mg/kg carbendazim | 505.2 | 484 | 438.3 | 499.8 | 492.2 | 480.1 |
| 5000 mg/kg carbendazim | 445.7 | 454.7 | 505.9 | 543.3 | 628.6 | 579.1 |
| 4000 mg/kg carbendazim | 481.5 | 511.5 | 543.1 | 552.9 | 507.8 | 560.3 |
| Mitoxantrone 1.5 mg/kg | 545.6 | 474.9 | 495.8 | 566.2 | 656.8 | 657.4 |

| dose | day 65 | day 68 | day 72 |
|---|---|---|---|
| peanut oil control | — | — | — |
| 6000 mg/kg carbendazim | 581.9 | 525.9 | 667.3 |
| 5000 mg/kg carbendazim | 562.3 | 562.3 | 602 |
| 4000 mg/kg carbendazim | 631.2 | 697.8 | 739.1 |
| Mitoxantrone 1.5 mg/kg | 775.1 | 820.8 | 707 |

Both the Cytoxan and the carbendazim were given p.o. twice a week

| dose | day 1 | day 5 | day 8 | day 12 | day 15 | day 19 |
|---|---|---|---|---|---|---|
| peanut oil control | 66.9 | 118.2 | 185.8 | 250.2 | 264.5 | 351 |
| 6000 mg/kg carbendazim | 66.7 | 97.3 | 143 | 193.5 | 237.9 | 316.2 |
| 5000 mg/kg carbendazim | 67.9 | 84.9 | 126.8 | 152.8 | 184.2 | 199.5 |
| 4000 mg/kg carbendazim | 67.2 | 110.4 | 157.6 | 192.6 | 238.9 | 298.7 |
| Cytoxan 300 mg/kg | 66.7 | 98.4 | 179.4 | 234.6 | 259.7 | 278.1 |

| dose | day 22 | day 26 | day 29 | day 33 | day 36 | day 39 |
|---|---|---|---|---|---|---|
| peanut oil control | 416.1 | 446.2 | 555.3 | 802.7 | 868.4 | 1032.3 |
| 6000 mg/kg carbendazim | 331.5 | 371.7 | 421.7 | 517.2 | 529.9 | 595.2 |
| 5000 mg/kg carbendazim | 236.8 | 247.6 | 293.6 | 351.5 | 409.8 | 497.8 |
| 4000 mg/kg carbendazim | 330.5 | 347.9 | 346.6 | 421.1 | 464.9 | 517 |
| Cytoxan 300 mg/kg | 351.2 | 467.8 | 583.8 | 786.1 | 904.2 | 1143.5 |

In the Colon—HT29 mouse model carbendazim at doses of 4000, 5000 and 5 6000 (mg/kg given twice weekly) it is better than Cytoxan in this model. At a dose of 3000 (mg/kg given twice weekly) it is also better than Cytoxan.

The carbendazim and Cytoxan were given twice weekly.

| dose | day 1 | day 5 | day 8 | day 12 | day 16 | day 19 |
|---|---|---|---|---|---|---|
| peanut oil control | 53.5 | 67.1 | 98.6 | 154.6 | 187 | 236.3 |
| Cytoxan 300 mg/kg | 51.3 | 60.3 | 42 | 58.5 | 64 | 87.8 |
| 6000 mg/kg carbendazim | 53.5 | 55.8 | 45.2 | 62.8 | 46.4 | 59.4 |
| 5000 mg/kg carbendazim | 53.5 | 58 | 58 | 104.3 | 83.2 | 109.7 |
| 4000 mg/kg carbendazim | 51.3 | 63.8 | 59.7 | 85.8 | 81.1 | 119.4 |

| dose | day 23 | day 26 | day 29 | day 37 | day 40 |
|---|---|---|---|---|---|
| peanut oil control | 335.5 | 433.1 | 499.9 | 786.3 | 984.9 |
| Cytoxan 300 mg/kg | 137.7 | 174 | 252 | 407.3 | 503 |
| 6000 mg/kg carbendazim | 77 | 78.4 | 60 | 51.3 | 62.5 |
| 5000 mg/kg carbendazim | 129.2 | 149.4 | 133.3 | 185.6 | 185.1 |
| 4000 mg/kg carbendazim | 142.1 | 159.6 | 156.2 | 184.6 | 212.9 |

| dose | day 1 | day 6 | day 9 | day 13 | day 16 | day 20 |
|---|---|---|---|---|---|---|
| control-no treatment | 77.1 | 172.3 | 231.4 | 348.1 | 409.3 | 478.4 |
| peanut oil control | 75.8 | 172.2 | 218.2 | 300.3 | 344 | 460 |
| Cytoxan 300 mg/kg | 76.6 | 132.5 | 152.5 | 142.8 | 188.1 | 226 |
| 3000 mg/kg carbendazim | 75.8 | 108.1 | 110.4 | 141.4 | 152.3 | 121.7 |

| dose | day 23 | day 26 | day 29 |
|---|---|---|---|
| control-no treatment | 582.8 | 710.2 | 867.3 |
| peanut oil control | 540.8 | 701.5 | 863 |
| Cytoxan 300 mg/kg | 372.7 | 375 | 478 |
| 3000 mg/kg carbendazim | 141.8 | 173.5 | 209.5 |

In the Breast—MX-1 model, carbendazim at 4000, 5000, and 6000 (mg/kg, twice weekly) was dose responsive in slowing the growth of the tumor and was better than Cytoxan. It is also very effective in MCF-7L breast line. At a dose of 3000, (mg/kg given twice weekly) it was equivalent to Navelbine.

The Cytoxan and the carbendazim were given twice weekly, p.o.

| dose | day 1 | day 5 | day 8 | day 12 | day 15 |
|---|---|---|---|---|---|
| peanut oil control | 70.9 | 208.6 | 526 | 1153.6 | 2267.9 |
| Cytoxan 300 mg/kg | 70 | 32.9 | 4.2 | 3.2 | 0 |
| 6000 mg/kg carbendazim | 70.4 | 151.8 | 259.9 | 492.9 | 663.6 |
| 5000 mg/kg carbendazim | 70.1 | 157.4 | 272.1 | 535.9 | 856.4 |
| 4000 mg/kg carbendazim | 70.3 | 158 | 320.4 | 626.2 | 1126.5 |

When the tumor was shrunk with Taxol first and then the carbendazim therapy started when the tumor began to grow again on day 130, the carbendazim treatment was begun and the tumor subsequently shrunk to zero. The Navelbine was given 1.6 mg./kg, qd×5, i.p; the Taxol was given 16 mg/kg, qd×5, i.p; and the carbendazim was dosed twice weekly, p.o. The carbendazim treatment was better than Navelbine and as good as Taxol in this study.

| dose | day 1 | day 5 | day 8 | day 12 | day 15 |
|---|---|---|---|---|---|
| peanut oil control | 72.9 | 91.4 | 95.2 | 117.1 | 121.4 |
| 3000 mg/kg carbendazim | 70.8 | 98.7 | 90.8 | 110.1 | 106.8 |
| Navelbine | 68.1 | 95.3 | 83.2 | 106.1 | 116.3 |
| Taxol | 68.9 | 85.2 | 52.1 | 36.3 | 27.5 |

-continued

| dose | day 20 | day 23 | day 26 | day 29 | day 35 | day 37 |
|---|---|---|---|---|---|---|
| peanut oil control | 157.6 | 171.9 | 170.1 | 211.6 | 226.1 | 229.4 |
| 3000 mg/kg carbendazim | 112.5 | 137.4 | 127.9 | 135.2 | 140.1 | 137.9 |
| Navelbine | 135.3 | 160.5 | 157.9 | 162.8 | 195.8 | 212.2 |
| Taxol | 28.5 | 31.8 | 32.4 | 34.2 | 36.3 | 32.9 |

| dose | day 41 | day 44 | day 48 | day 51 | day 55 | day 58 |
|---|---|---|---|---|---|---|
| peanut oil control | 253.2 | 257.7 | 252.1 | 247.8 | 263.9 | 278.3 |
| 3000 mg/kg carbendazim | 129.2 | 128 | 134.6 | 111.9 | 98.7 | 107.9 |
| Navelbine | 223.1 | 217.4 | 237.3 | 222.3 | 255.8 | 251.6 |
| Taxol | 29.9 | 38.7 | 29.7 | 33.3 | 27.1 | 35.2 |

| dose | day 62 | day 65 | day 69 | day 72 | day 76 | day 79 |
|---|---|---|---|---|---|---|
| peanut oil control | 274.4 | 252.8 | 275.2 | 277.9 | 274.7 | 296.4 |
| 3000 mg/kg carbendazim | 102.3 | 103.7 | 85.1 | 81.4 | 75.2 | 66.1 |
| Navelbine | 254.2 | 257.3 | 306.1 | 301.9 | 307.6 | 340.7 |
| Taxol | 35.2 | 35.2 | 22.2 | 33.2 | 32.9 | 35.2 |

| dose | day 82 | day 85 | day 89 | day 93 | day 97 | day 100 |
|---|---|---|---|---|---|---|
| peanut oil control | 277.2 | 276.1 | 168.7 | 197.2 | 278.8 | 264.6 |
| 3000 mg/kg carbendazim | 66.3 | 61.9 | 18.1 | 39.3 | 53.9 | 54.2 |
| Navelbine | 322 | 352.1 | 249.9 | 314.9 | 375.6 | 368.6 |
| Taxol | 35.2 | 39.2 | 17 | 36.8 | 43.7 | 46.8 |

| dose | day 103 | day 105 | day 110 | day 113 | day 116 | day 119 |
|---|---|---|---|---|---|---|
| peanut oil control | 266.1 | 263.1 | 277.2 | 278.3 | 288.9 | 305.3 |
| 3000 mg/kg carbendazim | 49.7 | 52.4 | 52.4 | 49.9 | 51.3 | 43.7 |
| Navelbine | 399.3 | 391.1 | 418.8 | 440.6 | 544.4 | 491.9 |
| Taxol | 53 | 53.2 | 50.5 | 48.4 | 65.9 | 65.8 |

| dose | day 124 | day 131 | day 134 | day 137 | day 140 | day 144 |
|---|---|---|---|---|---|---|
| peanut oil control | 331 | 371.9 | 396.7 | 440.5 | 449.5 | 482.8 |
| 3000 mg/kg carbendazim | 43.7 | 49.2 | 47.1 | 53.9 | 49.4 | 52.2 |
| Navelbine | 514.9 | 607.3 | 741.5 | 692.6 | 687.4 | 772.3 |
| Taxol | 76.6 | 86.8 | 92.8 | 97.9 | 92.6 | 92.4 |

| dose | day 147 | day 152 | day 155 | day 158 | day 161 | day 165 |
|---|---|---|---|---|---|---|
| peanut oil control | 506.6 | 540.7 | — | | | |
| 3000 mg/kg carbendazim | 50.6 | 53.9 | 49.4 | 40.7 | 49.4 | 49.4 |
| Navelbine | 811 | 809.4 | — | | | |
| Taxol | 104.6 | 105.9 | 116 | 68 | 73.1 | 68 |

| dose | day 172 | day 175 | day 179 | day 182 | day 186 | day 189 |
|---|---|---|---|---|---|---|
| peanut oil control | | | | | | |
| 3000 mg/kg carbendazim | 61.2 | 64.6 | 69.6 | 66.3 | 74.1 | 81.3 |
| Navelbine | | | | | | |
| Taxol | 68 | 71.9 | 73.1 | 68.1 | 67.1 | 68.1 |

| dose | day 193 | day 196 | day 200 | day 207 | day 210 | day 214 |
|---|---|---|---|---|---|---|
| peanut oil control | | | | | | |
| 3000 mg/kg carbendazim | 78.6 | 92.2 | 96.7 | 117.3 | 126.2 | 137 |
| Navelbine | | | | | | |
| Taxol | 66.3 | 63.9 | 58.5 | 51.4 | 54.8 | 34.1 |

| dose | day 217 | day 221 | day 224 | day 228 | day 232 | |
|---|---|---|---|---|---|---|
| peanut oil control | | | | | | |
| 3000 mg/kg carbendazim | 142.1 | 162.3 | 167.3 | 175.8 | 209.3 | |
| Navelbine | | | | | | |
| Taxol | 27.5 | 20.8 | 20.8 | 20.8 | 0 | |

| dose | day 236 | day 239 | day 245 | day 249 |
|---|---|---|---|---|
| peanut oil control | | | | |
| 3000 mg/kg carbendazim | 145.7 | 136.3 | 158.7 | 197.1 |
| Navelbine | | | | |
| Taxol | 0 | 0 | 0 | 0 |

In a third study carbendazim was tested in mice MX-1 model with the mice receiving estrogen tablets. Estrogen accelerates the growth of the breast cancer. At doses of 2000, 4000 and 6000 (mg/kg given once weekly) it was better than both Navelbine (1.6 mg/kg, qd×5, i.p.) and Taxol (16 mg/kg, qd×5, i.p.) in this faster growing MX-1 cancer.

| dose | day 1 | day 5 | day 9 | day 12 | day 16 |
|---|---|---|---|---|---|
| peanut oil control | 109.2 | 307.7 | 947.6 | 1702.8 | 3359.8 |
| 6000 mg/kg carbendazim | 109.5 | 292.7 | 593.1 | 1279.6 | 1261.6 |
| 4000 mg/kg carbendazim | 109.5 | 337.1 | 664.2 | 1143.3 | 1501.5 |
| 3000 mg/kg carbendazim | 110.4 | 312.4 | 603.6 | 1068 | 1502.6 |
| 2000 mg/kg carbendazim | 110.4 | 342.3 | 752.3 | 1447.6 | 1609.1 |
| Navelbine | 110.2 | 278.6 | 874.5 | 1528.5 | 2746.8 |
| Taxol | 110.4 | 292.7 | 484.9 | 876.6 | 1941.5 |

In the Pancreas (Mia-PaCa) model, carbendazim at 3000 and 4000 (mg/kg, twice weekly) is as good as or better than gemcitabine. At 2000 mg/kg the carbendazim was not as effective after 21 days. Gemcitabine was given on days 1,4,7 and 10 i.p.; the carbendazim was given p.o. twice weekly.

| dose | day 1 | day 5 | day 9 | day 12 | day 16 |
|---|---|---|---|---|---|
| peanut oil control | 63.1 | 118.5 | 186.6 | 228.4 | 294.6 |
| 4000 mg/kg carbendazim | 64 | 78.9 | 121.3 | 113.4 | 133.4 |
| 3000 mg/kg carbendazim | 63.1 | 71.8 | 100.1 | 100.4 | 139.6 |
| 2000 mg/kg carbendazim | 63.7 | 85.2 | 128.4 | 155.1 | 213.4 |
| Gemcitibine - 80 mg/kg | 63.9 | 71.7 | 81.7 | 77.1 | 94.9 |

| dose | day 19 | day 23 | day 26 | day 30 | day 33 | day 37 |
|---|---|---|---|---|---|---|
| peanut oil control | 325.9 | 462.8 | 489.5 | 546.6 | | |
| 4000 mg/kg carbendazim | 119.4 | 157 | 154.2 | 124.3 | 131.4 | 129.2 |
| 3000 mg/kg carbendazim | 131.9 | 146.6 | 131.9 | 140.1 | 135.1 | 110.6 |
| 2000 mg/kg carbendazim | 182.2 | 185 | 189.9 | 214.1 | 206.7 | 217.6 |
| Gemcitibine - 80 mg/kg | 111.3 | 167.1 | 204 | 258.7 | 330.3 | 404.3 |

| dose | day 40 | day 44 | day 47 | day 51 | day 54 | day 61 |
|---|---|---|---|---|---|---|
| peanut oil control | | | | | | |
| 4000 mg/kg carbendazim | | | | | | |
| 3000 mg/kg carbendazim | 105 | 105 | 120.1 | 124.1 | 124.1 | 118.6 |
| 2000 mg/kg carbendazim | 214.55 | 214.5 | 210.9 | 222.4 | 225.6 | 214.1 |
| Gemcitibine - 80 mg/kg | 503.7 | | | | | |

| dose | day 65 | day 68 | day 72 | day 75 | day 79 |
|---|---|---|---|---|---|
| peanut oil control | | | | | |
| 4000 mg/kg carbendazim | | | | | |
| 3000 mg/kg carbendazim | 130 | 130 | 69.2 | 52.5 | 75.8 |
| 2000 mg/kg carbendazim | 217.3 | 217.3 | 202.6 | 178.2 | 169.7 |
| Gemcitibine - 80 mg/kg | | | | | |

In the Panc-01 model for pancreatic cancer carbendazim at a dose of 5000 mg/kg was better than Gemcitabine at 32 days. The Gemcitabine is given i.p., q3d×4 and the carbendazim is given p.o. twice weekly to the end.

| dose | day 1 | day 4 | day 8 | day 11 | day 18 | day 22 | day 25 | day 29 | day 32 |
|---|---|---|---|---|---|---|---|---|---|
| control - no treatment | 64.1 | 110.8 | 201.5 | 339.7 | 726 | 1001.4 | 1183 | | |
| peanut oil control | 64.3 | 123.8 | 200.3 | 306 | 740.3 | 1174.1 | 1126.7 | | |
| Gemcitabine 80 mg/kg | 64 | 106.3 | 171.7 | 248.5 | 561.4 | 943.6 | 1053 | 1183 | |
| 5000 mg/kg carbendazim | 64.4 | 115.5 | 166.8 | 247 | 417.9 | 574.3 | 695.8 | 845 | 807.9 |

In the Neuroblastoma (SK-N-MC) model a decrease in tumor growth at 5000 (mg/kg) is shown and there is favorable activity early in the study compared to topotecan. It is expected, based on learning from the other studies, that a lower dose would be effective. The topotecan is given i.p. qd×5 and the carbendazim is given p/.o. twice weekly.

In the Lung cancer model MV522 all groups received Taxol and then received treatments shown starting 10 days later. At doses of 2000, 3000, 4000 and 5000 (mg/kg given twice weekly, p.o.) tumor growth was suppressed in a dose response and the tumor was shrunk in the 5000 mg/kg group. Day 1 is the start of the treatment with carbendazim.

| dose | day 1 | day 5 | day 9 | day 12 | day 16 | day 19 | day 23 | day 25 | day 31 |
|---|---|---|---|---|---|---|---|---|---|
| peanut oil control | 454.8 | 1034.1 | 1533.1 | 1141.8 | 1402 | 1668.2 | 1852.8 | 2025 | |
| 5000 mg/kg carbendazim | 474.4 | 505.8 | 799.3 | 841.8 | 732 | 1424.3 | 1480.5 | 936 | |
| Topotecan 3 mg/kg | 504.9 | 209.8 | 57.5 | 71.8 | 144.7 | 294.6 | 648.1 | 886.6 | 1150.2 |

In the Rhabdomysarcoma model, a childhood cancer, at day 29 carbendazim at doses of 3000, 4000 and 5000 (mg/kg given once weekly, p.o.) is quite effective against this tumor with no toxicity in the 3000 (mg/kg) group. Topotecan (i.p., qd×5) is quite active against this model.

| dose | day 1 | day 5 | day 8 | day 12 | day 15 |
|---|---|---|---|---|---|
| peanut oil control | 58.1 | 121.3 | 177 | 223 | 340.9 |
| 5000 mg/kg carbendazim | 58.1 | 95.1 | 87 | 88.1 | 106.4 |
| 4000 mg/kg carbendazim | 59.5 | 110.7 | 124.2 | 121.6 | 155.3 |
| 3000 mg/kg carbendazim | 58.2 | 110.4 | 136.6 | 176.7 | 248.2 |
| Topotecan 3 mg/kg | 58.3 | 82 | 53.3 | 24.1 | 26.6 |

| dose | day 19 | day 22 | day 26 | day 29 | day 35 | day 37 |
|---|---|---|---|---|---|---|
| peanut oil control | 558 | 689.3 | 894 | 948.3 | 1038.2 | 1098.5 |
| 4000 mg/kg carbendazim | 112.6 | 107.9 | 137.5 | 174.3 | 238.8 | 317.4 |
| 3000 mg/kg carbendazim | 113 | 127 | 140.8 | 144.3 | 131.9 | 152.4 |
| 2000 mg/kg carbendazim | 313.1 | 291.2 | 384.3 | 417.4 | 591.2 | 492.9 |
| Topotecan 3 mg/kg | 13.4 | 18.9 | 40.9 | 64.2 | 107.9 | 158.9 |

| dose | day 40 | day 43 | day 47 |
|---|---|---|---|
| peanut oil control | | | |
| 4000 mg/kg carbendazim | 313.9 | 423 | 171.5 |
| 3000 mg/kg carbendazim | 142.6 | 195.5 | 235.8 |
| 2000 mg/kg carbendazim | 555.6 | 682.1 | 854.3 |
| Topotecan 3 mg/kg | 184.4 | 279.2 | 351.9 |

| dose | day 1 | day 4 | day 8 | day 11 | day 15 | day 18 |
|---|---|---|---|---|---|---|
| control - no treatment | 6.6 | 5.6 | 7.3 | 18.3 | 39.6 | 80.2 |
| peanut oil control | 6.7 | 16.9 | 29.7 | 50.6 | 84.9 | 140.6 |
| 5000 mg/kg carbendazim | 6.5 | 7.1 | 16.1 | 12.7 | 18.8 | 27.2 |
| 4000 mg/kg carbendazim | 6.6 | 8.5 | 17.6 | 16.2 | 20.7 | 26.6 |
| 3000 mg/kg carbendazim | 6.5 | 7.1 | 11.9 | 9.2 | 14.1 | 16 |
| 2000 mg/kg carbendazim | 6.5 | 10.3 | 19.9 | 33.8 | 44.8 | 40.5 |

| dose | day 22 | day 25 | day 29 | day 32 | day 36 |
|---|---|---|---|---|---|
| control - no treatment | 128.8 | 180.1 | 270.7 | 307.3 | 594.6 |
| peanut oil control | 233.9 | 341.4 | 488.7 | | |
| 5000 mg/kg carbendazim | 21.5 | 31.4 | 40.5 | 29.5 | 54 |
| 4000 mg/kg carbendazim | 40.8 | 39.7 | 58.9 | 47.3 | 62.5 |
| 3000 mg/kg carbendazim | 19.9 | 23.4 | 37.5 | 28.9 | 44.5 |
| 2000 mg/kg carbendazim | 37.9 | 43.5 | 49.8 | 41.1 | 53 |

| dose | day 39 | day 42 | day 46 | day 49 | day 52 | day 56 |
|---|---|---|---|---|---|---|
| control - no treatment | 572.4 | 670.1 | | | | |
| peanut oil control | | | | | | |
| 5000 mg/kg carbendazim | 63 | 86.8 | 86 | 1 | 0.5 | |
| 4000 mg/kg carbendazim | 62.5 | 32 | | | | |
| 3000 mg/kg carbendazim | 59.2 | 69.3 | 72.6 | 160.7 | 207.1 | 267.4 |
| 2000 mg/kg carbendazim | 42.9 | 47.1 | 60.3 | 107.4 | 107.4 | 175.3 |

| dose | day 59 | day 63 | day 66 |
|---|---|---|---|
| control - no treatment | | | |
| peanut oil control | | | |
| 5000 mg/kg carbendazim | | | |
| 4000 mg/kg carbendazim | | | |
| 3000 mg/kg carbendazim | 75.4 | 77 | 94.5 |
| 2000 mg/kg carbendazim | 214.9 | 193.7 | 188.9 |

In a Medulloblastoma model (IMR32) a dosage dependent effect is seen with carbendazim at doses of 5000, 4000, and 3000 (mg/kg, p.o. twice weekly). It is compared with Topotecan (i.p. qd×5).

| dose | day 1 | day 7 | day 9 | day 12 | day 15 | day 19 |
|---|---|---|---|---|---|---|
| peanut oil control | 57.6 | 82.1 | 103.8 | 107.5 | 143.1 | 182.7 |
| 5000 mg/kg carbendazim | 57.2 | 74.9 | 86.4 | 94.6 | 102 | 125.4 |
| 4000 mg/kg carbendazim | 58.1 | 89.3 | 108 | 112.9 | 152.9 | 162.3 |
| 3000 mg/kg carbendazim | 58.1 | 73.8 | 99.3 | 105.1 | 119.7 | 153.4 |
| Topotecan 3 mg/kg | 57.8 | 22.6 | 23.6 | 15.7 | 3.6 | |

In the Murine Melanoma—B16 mice model doses of 4000, 5000 and 6000 (mg/kg) were at least equal in tumor suppression compared to cytoxan at 30–60 days. Since this tumor is a liquid tumor, there is no change in tumor weight. The results are summarized in Table 1 below.

In the P-388 model for leukemia there was a dose responsive effect and the results were good. See Tables 2 and 3.

The data in Tables 1, 2 and 3 are reported in T/C which is interpreted using the following scale:

| T/C < 125 | no activity |
|---|---|
| T/C = 125–150 | weak activity |
| T/C = 150–200 | modest activity |
| T/C = 200–300 | high activity |
| T/C = 300 with long term survivors | excellent activity | long term survivors for P388 is >30 days, for B16 it is >60 days. The NCI Measure of Success is T/C=125.

Use of Carbendazim in the treatment of B16

This study was performed in black mice injected i.p. with B-16 mouse melanoma which many researchers believe is the most predictive model for efficacy in humans. Carbendazim was equally effective as Cytoxan in this model at treating B-16. The activity is dose responsive. Death is the end point in this model.

TABLE 1

| Dosage (mg/kg) twice weekly | T/C | weight change (%) | Positive Control |
|---|---|---|---|
| 5000 | 198 | −0.64 | Cytoxan at 300 mg/kg |
| 2500 | 169 | +3.16 | on dose |
| 2000 | 169 | −11.63 | T/C 191, −8.43% |
| 1250 | 124 | +1.99 | weight change |
| 1000 | 176 | −4.75 | |
| 500 | 141 | −0.64 | |

TABLE 2

In a repeat test the following results were achieved:

| Dosage (mg/kg) twice weekly | T/C | weight change (%) | Positive Control |
|---|---|---|---|
| 6000 | 183 | −0.38 | Cytoxan at 300 mg/kg |
| 5000 | 167 | −1.44 | one dose |
| 4000 | 138 | +3.86 | T/C 161, −4.28% weight change |

TABLE 3

Use of Carbendazim in the treatment of P388

| Dosage (mg/kg) | T/C | weight change (%) | Positive Control |
|---|---|---|---|
| 4000 | 189 | −9 | cytoxan at 125 mg/kg |
| 2000 | 148 | +8 | is curative; weight |
| 1000 | 129 | +15 | change −14 |

Accordingly, carbendazim retards the growth of both solid and liquid tumors in vivo.

These studies confirm previous in vivo studies in which carbendazim was tested in various in vivo models for different types of cancer.

Additional in vivo cancer studies are presented in a tabular form below. The data is presented in the following format—dose regimen in parenthesis, dosage in mg/kg: tumor growth suppression (tg supp.), toxic deaths/number of test subjects (deaths), % weight change (wt).

TABLE 4

| Cancer | | | | Positive Control | | | |
|---|---|---|---|---|---|---|---|
| dose | tg supp. | deaths | wt. | dose | tg supp. | deaths | wt. |
| MX1 xenograft - (twice weekly) | | | | Cytoxan (1 dose) | | | |
| 6000 | 70% | 1/9 | −4 | 300 | complete shrinkage | 0/10 | −7 |
| 5000 | 63% | 1/10 | −4 | | | | |
| 4000 | 48% | 0/10 | −1 | NCI Measure of Success: 58% | | | |
| MCF-7L (breast) (twice weekly) | | | | Cytoxan (1 dose) | | | |
| 6000 | | 10/10 | | 300 | 100% | 3/10 | −15 |
| 5000 | 100% | 7/10 | −8 | NCI Measure of Success: 58% | | | |
| 4000 | 94% | 5/10 | −7 | | | | |
| DU-145 (twice weekly) | | | | Cytoxan (1 dose) | | | |
| 6000 | 33% | 1/10 | −6 | 300 | 0% | 0/10 | +6 |
| 5000 | 48% | 1/10 | −8 | | | | |
| 4000 | 52% | 0/10 | −5 | NCI Measure of Success: 58% | | | |
| A549 (lung) | | | | Cytoxan | | | |
| 2500 | | 10/10 | | 125 | 69% | 0/10 | −1 |
| 500 | 57% | 0/10 | +10 | | | | |
| HT29 (colon) (twice weekly) | | | | Cytoxan (1 dose) | | | |
| 6000 | 97% | 9/10 | −25 | | | | |
| 5000 | 79% | 2/10 | −8 | | | | |
| 4000 | 78% | 3/10 | −12 | 300 | 45% | 0/10 | +10 |
| 3000 | 65% | 2/10 | −6 | | | | |
| 2000 | 36% | 0/10 | +3 | NCI Measure of Success: 58% | | | |
| SK-MES (twice weekly) | | | | Taxol (5 doses) | | | |
| 6000 | 69% | 3/10 | −2 | 20 | 75% | 0/10 | +1 |
| 5000 | 44% | 1/10 | +2 | | | | |
| 4000 | 45% | 2/10 | +3 | | | | |
| | | | | Navelbine (5 doses) | | | |
| | | | | 2 | 26% | 1/10 | −5 |
| | | | | NCI Measure of Success: 58% | | | |

Carbendazim demonstrated the ability to reduce tumor growth in mice models for breast, lung, colon, murine melanoma and leukemia. The data are summarized in Table 5 and Table 6 below.

TABLE 5

| Cancer | Dosage | Tumor Growth Decrease (%) | Positive Control (Dosage in mg/kg) | Tumor Growth Decrease |
|---|---|---|---|---|
| MX1-breast | 500 mg/kg | 42% | cytoxan (125) | regression |
|  | 2500 mg/kg | 37% |  |  |
| A549-lung | 500 mg/kg* | 57% | cytoxan (125) | 69% |
| HT29-colon | 2500 mg/kg** | 54% | cis-plat (4) | 59% |

*in this model 2500 mg/kg was toxic; **in this model 500 mg had no effect

In the same test 2-(4-thiazolyl)-1-H-benzimidazole showed no activity against MX1 breast cancer tumors implanted subcutaneously under the mice skin.

TABLE 6

| Cancer | Dosage | Increased Life Span | Positive Control |  |
|---|---|---|---|---|
| P388-luekemia | 1000 mg/kg | 129% | cytoxan (125) | curative |
|  | 2000 mg/kg | 148% |  |  |
|  | 4000 mg/kg | decreased life span - 9% |  |  |
| B16 melanoma | 1000 mg/kg | 131% | navelbine (2) | increased life span - 265% |
|  | 2000 mg/kg | 163% |  |  |
|  | 4000 mg/kg | 187% |  |  |

In the same test 2-(4-thiazolyl)-1-H-benzimidazole showed no activity against P388.
In the same test 2-(4-thiazolyl)-1-H-benzimidazole showed no activity against B16.

The in vivo and in vitro data support the assertion that carbendazim has broad scale efficacy against multiple cancer types.

Initial efficacy of carbendazim appears to be comparable to the best available drugs used for the treatment of any particular cancer type. Furthermore, with continuous treatment, breast cancers do not come back as usually happens with cytoxan and taxol in breast cancer or gemcitabine in pancreatic cancer.

It is equally effective against p53 deficient/defective cell lines, unlike most existing cancer treatment drugs.

It is excellent in B16 mouse melanoma, which is believed by many people to be the best predictive model for efficacy in humans.

These same benzimidazole derivatives are effective against viruses including HIV, influenza, rhinoviruses and herpes viruses. The benzimidazole derivatives can be used alone or in combination with other fingicides.

The following examples illustrate the effectiveness of thiabendazole, 2-(4-thiazolyl)-1-H-benzimidazole, against HIV and the benzimidazoles derivatives against a number of viruses.

The results of these HIV studies are summarized in more detail below:

Thiabendazole is effective at totally suppressing virus production in chronically infected cells. The extra cellular viral count goes effectively to zero or nondetectable levels. Thiabendazole does not kill the chronically infected cells though it does reduce the rate of cell proliferation at active concentrations. Thiabendazole does not affect $CD_4$ expression in uninfected cells. At effective concentrations thiabendazole slows but does not alter the normal cellular RNA or protein synthesis of either infected or non-infected cells. Thiabendazole is effective in a variety of chronically infected cell types (this effect is not cell type specific.)

Thiabendazole is effective as a variety of HIV virus strains. (Not virus strain specific—although some variance by strain is observed; SK-1>IIIB>RF) Also thiabendazole is not effective on HIV in vitro or in vivo.

After 20 months no resistant virus strains to thiabendazole have developed in tests designed to do so. Resistance develops in six months or less in this test for existing IV drugs with resistance strains for protease inhibitors developing in about 3–4 months.

Thiabendazole does not adversely affect the activity of existing HIV drugs, AZT, 3TC, ddC, ddI or protease inhibitors (saquinavir and indinavir) in acutely infected cells, nor do any of these Ewing drugs interfere with the efficacy of thiabendazole in chronically infected cells. It is used in combination with these drugs. Thiabendazole is also effective against protease inhibitor resistant viruses.

Thiabendazole confers temporary suppression of viral production from 4 to 80 days after treatment stops. This is unique and a useful feature whenever one has problems with compliance.

The results of these studies are summarized in detail below:

HIV Virus Replication Study

Thiabendazole was tested in chronically infected HIV virus. These cell populations contain integrated copies of the HIV genome and constituitively produce HIV at relatively high levels (CEM-SK1, U937-SK1 and H9-SK1 from Frederick Research Center, Maryland) or are latently infected and only produce virus after stimulation with phorbol esters, tumor necrosis factor or IL6 (U1 and ACH2). Virus production was reduced in all cell lines tested and thiabendazole did not stimulate virus production from the latently infected cells. Reductions in virus production were observed when quantifying supernatant reverse transcriptase activity, supernatant p24 as well as intracellular p24, indicating the compound inhibits virus production at a step of replication prior to production of intracellular proteins.

Quantification of the infectivity of virions produced from the infected cells demonstrates reductions in the number of infectious virions in parallel with reductions in supernatant RT or p24, indicating the compound reduces the amount of virus produced, but not the quality of the virions. Inhibition of virus production from the chronically infected cells was observed at concentrations which were nontoxic to the target class. Thiabendazole inhibited virus production at concentrations greater than 1–10 µg/ml.

Toxicity to the chronically infected cells was similar to that observed with the uninfected cells. Evaluation of thiabendazole on chronically infected cells was performed by evaluation of thymidine (DNA), uridine (RNA) and leucine (protein) incorporation into cellular macromolecules. Inhibition of cellular macromolecule synthesis paralleled the toxicity of the compound as would be expected and did not occur at lower nontoxic concentrations found to inhibit virus production from the chronically infected cells.

After 28 days of treatment on chronically infected cells, the toxicity of the compound to the target cells appeared similar in both uninfected and chronically infected cells. The compound does not preferentially kill HIV-infected cells. Reductions in the level of virus production were stable and were observed at concentration greater than 10 µg/ml for thiabendazole.

These results suggest thiabendazole can quickly reduce the level of virus production from cell populations chronically infected with HIV-1 and the antiviral effect is maintained with prolonged compound exposure. This reduction of virus production occurs at concentrations which are nontoxic to the host cell and which have no effect on the synthesis of cellular DNA, RNA and protein.

Virus Resistance Studies

Chronically infected HIV cells were cultured in the presence of thiabendazole at 1 µg/ml for the first month, 5 µg/ml for the second month, 10 µg/ml for the third month, 20 and 40 µg/ml for the fourth month and 80 µg/ml for the fifth and sixth months. At the end of each month, the cells were evaluated for virus production compared to chronically infected cells not treated with the compound. For each of the six months of treatment experience, no change in the antiviral effect of the compound was noticed and the toxicity of the compound remains identical. Thiabendazole remains active against HIV and that resistance was not rapidly achieved via the selection of resistant viruses or adaptation of the cells to prevent compound induced toxicity. Virus production remains totally suppressed from cultures treated with thiabendazole at 40 and 80 µg/ml.

The present invention includes a method of treatment HIV with the benzimidazole compounds without inducing formation of benzimidazole derivative or thiabendazole resistant HIV.

Reappearance of Virus Production from Chronically Infected Cells Previously Treated Chronically infected cells which were treated with compound for prolonged periods were washed free of compound and cultured to determine if, and when, virus production would resume. Cultures in which treatment resulted in the total elimination of virus production were used in these assays. These cultures included chronically infected cells cultured in the presence of 20, 40, and 80 µg/ml of thiabendazole. Within 4 days virus production resumed from the cells cultured in the presence of the lower concentrations of thiabendazole (20 µg/ml and 4 µg/ml). Virus production resumed at the 40 µg/ml concentration of thiabendazole by day 12. At the highest concentrations virus production was observed at approximately day 70.

The present invention includes a method of treatment HIV with the benzimidazole derivative or thiabendazole and delaying the reappearance of HIV in plasma following initial treatment of HIV with an antiviral agent or thiabendazole.

Infectability of Cells Treated with Thiabendazole

Cells which were pretreated with thiabendazole for a long period of time were washed free of compound and used as a target cell population. The cells were split into 3 populations and labeled Group 1, 2 or 3. Group 1 was treated with the compound for 24 hours (at the same concentration used in the prolonged treatment phase), washed free of compound and cultured in the presence of infectious virus and fresh compound. Group 2 was pretreated for 24 hours, washed free of compound and cultured in the presence of infectious virus only. Group 3 was cultured for both the pretreatment and the infection phases in fresh medium only (no virus or compound). Virus production from the cell populations was identical irrespective of the culture conditions. These results indicate that the chronically infected cells treated for prolonged periods were not superinfected with HIV.

ADDITIONAL CHRONIC HIV STUDIES

Chronic HIV-1 infected cells U1 were derived from an acute HIV-1 infection of the promonocytic cell line, U937. The chronic HIV-1 infected cells, ACH-2 were derived from an acute HIV-1 infection of the T cell line, A3.01.

These cells were cultured in medium and the phorbol ester, PMA. PMA causes the cells (both U1 and ACH-2) to be activated and not divide but it also causes the U-1 cells to differentiate. This results in fewer cells in the PMA-treated cultures than the media alone cultures. Cell viability was measured when these cell lines were treated with the test compound.

Both cell lines constituitively produce a small amount of HIV-1. ACH-2 cell lines tend to produce more HIV-1 than U1 cells as shown by p24 ELISA. When either cell line is cultured in the presence of PMA there is an increase in the quantity of HIV-1 produced as measured by the p24 antigen ELISA.

In addition, the number of institute positive HIV mRNA expressing cells per microscopic field is measured. Comparisons can be made from these numbers since the same number of cells were adhered to the glass slides for each drug concentration $10 \times 10^6$ cells/ml).

These cells were treated with test samples. Thiabendazole at 60 µg/ml suppressed replication in the HIV monocytes by 74% and the T-cell HIV replication was increased by 26%. The positive control was interferon which suppressed HIV monocytes replication by 80%. AZT showed no activity in this model.

2-(Methoxycarbonylamino)benzimidazole suppressed replication in the HIV monocytes by 9% and the T-cell HIV replication was increased by 44%. The positive control was interferon which suppressed HIV monocytes replication by 80% and suppressed T-cell HIV replication by 60%.

Acute HIV Testing

In an in vitro acute model for HIV 2-methoxycarbonylamino)benzimidazole inhibited viral replication by 100% at 4 µg/ml and AZT inhibited viral replication by 98% at 1 µg/ml. 2-(4-thiazolyl)-1-H-benzimidazole inhibited viral replication by 98% at 60 µg/ml.

The therapeutic index (TI), the ratio of the toxic dose of drug to efficacious dose of drug for 2-(4-thiazolyl)-1-H-benzimidazole is 2.8 versus 12, 500 for AZT. The TI for 2-(methoxycarbonylamino)benzimidazole is 1.8.

In vivo Herpes

In an in vivo herpes screening test of 2-(4-thiazolyl)-1-H-benzimidazole at a dose of 200 mg/kg dose, 10% of the mice survived with a 10.4 mean death date; at 100 mg/kg dose 50% of the mice survived with a 9.2 mean death date. The positive control was acyclovir at 75 mg/kg dose; 60% of the mice survived with a mean death date of 17.2 days. In the same test 2-(methoxycarbonylamino)benzimidazole showed no activity.

Other Tests

Both 2-(4-thiazolyl)-1-H-benzimidazole and 2-methoxycarbonylamino) benzimidazole were tested in an in vitro influenza model and showed no activity.

In an in vivo model for influenza 2-(4-thiazolyl)-1-H-benzimidazole was tested at 200 mg/kg, 67% of the mice survived with a mean death date of 8 days; at 100 mg/kg, 62% survived with a mean death date of 8.7 days. The positive control was amantadine (75 mg/kg) with 100% of the mice surviving for 21 days. 2-(Methoxycarbonylamino) benzimidazole was not active in the same test.

Both 2-(4-thiazolyl)-1-H-benzimidazole and 2-(methoxycarbonylamino) benzimidazole were tested in an in vitro herpes model and showed no activity.

Both 2-(4-thiazolyl)-1-H-benzimidazole and 2-(methoxycarbonylamino) benzimidazole were tested in an in vitro rhinovirus model and compared to A-36683. The therapeutic index (TI), the ratio of the toxic dose of drug to efficacious dose of drug, for 2-(4-thiazolyl)-1-H-benzimidazole is 1–2 and for 2-(methoxycarbonylamino) benzimidazole is 1–3 versus 1000–3200 for A36683.

The demonstrated effectiveness of the compounds of the present invention in the human breast and lung tumor xenograft models indicate that the compounds of the present invention are useful for the treatment of solid tumors in man, and, in particular, tumors of the breast and lung. This conclusion is further supported by published analyses correlating preclinical test results with clinical efficacy of anti cancer agents. For example, see: Goldin and Venditti (1 980) Recent Results Cancer Research 76: 176–191; Goldin et al. (1981) Eur. J. Cancer 17: 129–142; Mattern et al. (1988) Cancer and Metastasis Review 7: 263–284; Jackson et al. (1990) Cancer Investigations 8: 39–47. Based on these published analyses, the exceptional high level of antitumor activity exhibited by the presently claimed compounds provide strong evidence that the compounds claimed in present invention have therapeutic utility in the treatment of cancer in man and that they will improve the quality of life of the patient.

What is claimed is:

1. A method of treating a viral infection in mammals comprising administering to a mammal in need thereof a therapeutically effective amount of a benzimidazole derivative of the following formula:

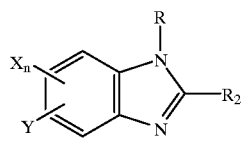

wherein,

X is hydrogen, halogen, alkyl of less than 7 carbon atoms, or alkoxy of less than 7 carbon atoms;

n is a positive integer of less than 4;

Y is hydrogen, chloro, nitro, methyl, ethyl, or oxychloro;

R is hydrogen, an alkyl group of from 1 to 8 carbon atoms, or alkylaminocarbonyl wherein the alkyl group has from 3 to 6 carbon atoms; and $R_2$ is 4-thiazolyl or $NHCOOR_1$ wherein $R_1$ is an aliphatic hydrocarbon of less than 7 carbon atoms.

2. A method according to claim 1 wherein said benzimidazole derivative has the formula:

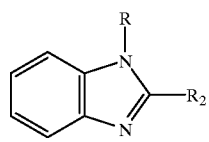

wherein

R is hydrogen, an alkyl having from 1 to 8 carbon atoms, or $CONHR_3$ wherein $R_3$ is alkyl of less than 7 carbons; and $R_2$ is selected from the group consisting of 4-thiazolyl and $NHCOOR_1$, wherein $R_1$ is methyl, ethyl or isopropyl.

3. A method according to claim 1 wherein the virus causing said viral infection is a retrovirus.

4. A method according to claim 1 wherein the virus causing said viral infection is herpes simplex.

5. A method according to claim 1 wherein the virus causing said viral infection is HIV.

6. A method according to claim 1 wherein the virus causing said viral infection is a rhinovirus.

7. A method according to claim 1 wherein said benzimidazole derivative is in the form of a prodrug.

8. A method according to claim 1 wherein said benzimidazole derivative is in the form of a pharmaceutically acceptable salt thereof.

9. A method according to claim 8 wherein said pharmaceutically acceptable salt is selected from the group consisting of chlorides, bromides sulfates, nitrates, phosphates, sulfonates, formates, tartrates, maleates, malates, citrates, benzoates, salicylates, ascorbates, and mixtures thereof.

10. A method according to claim 9 wherein said pharmaceutically acceptable salt is a hydrochloride salt.

11. A method according to claim 1 wherein said benzimidazole derivative is administered in an amount of from 30 mg per kg body weight to 10,000 mg per kg body weight.

12. A method according to claim 1 wherein said benzimidazole derivative is in a liquid dosage form comprising a pharmaceutical carrier selected from the group consisting of a solution, an emulsion, a suspension, solution, a suspension reconstituted from a non-effervescent or an effervescent preparation, and a suspension in a pharmaceutical acceptable fat or oil.

13. A method according to claim 1 wherein said benzimidazole derivative is in a solid dosage form comprising a pharmaceutical carrier selected from the group consisting of lactose, sucrose, gelatin, and agar.

14. A method according to claim 1 wherein said benzimidazole derivative is in the form of a liposome delivery system.

15. A method according to claim 1 wherein said benzimidazole derivative is coupled to a soluble polymer.

16. A method according to claim 1 wherein said benzimidazole derivative is coupled to a biodegradable polymer.

17. A method of treating a viral infection in mammals comprising administering to a mammal in need thereof a therapeutically effective amount of 2-(4-thiazolyl)-1-H-benzimidazole.

18. A method according to claim 17 wherein said 2-(4-thiazolyl)-1-H-benzimidazole is in the form of a prodrug.

19. A method according to claim 17 wherein said 2-(4-thiazolyl)-1-H-benzimidazole is in the form of a pharmaceutically acceptable salt thereof.

20. A method according to claim 19 wherein said pharmaceutically acceptable salt is selected from the group consisting of chlorides, bromides, sulfates, nitrates, phosphates, sulfonates, formates, tartrates, maleates, malates, citrates, benzoates, salicylates, ascorbates, and mixtures thereof.

21. A method according to claim 19 wherein said pharmaceutically acceptable salt is a hydrochloride salt.

22. A method according to claim 17 wherein said 2-(4-thiazolyl)-1-H-benzimidazole is administered in an amount of from 30 mg per kg body weight to 10,000 mg per kg body weight.

23. A method according to claim 17 wherein said 2-(4-thiazolyl)-1-H-benzimidazole is in a liquid dosage form comprising a pharmaceutical carrier selected from the group consisting of a solution, an emulsion, a suspension, solution, a suspension reconstituted from a non-effervescent or an effervescent preparation, and a suspension in a pharmaceutical acceptable fat or oil.

24. A method according to claim 17 wherein said 2-(4-thiazolyl)-1H-benzimidazole is in a solid dosage form comprising a pharmaceutical carrier selected from the group consisting of lactose, sucrose, gelatin, and agar.

25. A method according to claim 17 wherein said 2-(4-thiazolyl)-1-H-benzimidazole is in the form of a liposome delivery system.

26. A method according to claim 17 wherein said 2-(4-thiazolyl)-1-H-benzimidazole is coupled to a soluble polymer.

27. A method according to claim 17 wherein said 2-(4-thiazolyl)-1-H-benzimidazole is coupled to a biodegradable polymer.

28. A method according to claim 17 wherein the virus causing said viral infection is a retrovirus.

29. A method according to claim 17 wherein the virus causing said viral infection is herpes.

30. A method according to claim 17 wherein the virus causing said viral infection is HIV.

31. A method according to claim 17 wherein the virus causing said viral infection is a rhinovirus.

32. A method according to claim 17 wherein the virus causing said viral infection is influenza.

33. A method according to claim 1 wherein the virus causing said viral infection is influenza.

34. A method according to claim 1 wherein said benzimidazole derivative is methyl 1-(butylcarbamoyl)-2-benzimidazolecarbamate or 2-methoxycarbonylaminobenzimidazole.

35. A method according to claim 34 wherein said benzimidazole derivative is in the form of a hydrochloride salt.

36. A method according to claim 34 wherein said benzimidazole derivative is in the form of a prodrug.

37. A method according to claim 1 wherein said benzimidazole derivative is 2-methoxycarbonylaminobenzimidazole and wherein the virus causing said viral infection is HIV.

38. A method according to claim 37 wherein said 2-methoxycarbonylaminobenzimidazole is administered in an amount of from about 150 mg per kg body weight to about 6000 mg per kg body weight.

39. A method according to claim 37 wherein said 2-methoxycarbonylaminobenzimidazole is in the form of a hydrochloride salt.

40. A method according to claim 37 wherein said 2-methoxycarbonylaminobenzimidazole is micronized.

41. A method according to claim 37 wherein said 2-methoxycarbonylaminobenzimidazole is in the form of a prodrug.

* * * * *

UNITED STATES PATENT AND TRADEMARK OFFICE
CERTIFICATE OF CORRECTION

PATENT NO. : 6,362,207 B1 Page 1 of 1
DATED : March 26, 2002
INVENTOR(S) : James Berger Camden It is certified that error appears in the above-identified patent and that said Letters Patent is hereby corrected as shown below:

Column 28,
Line 3, insert -- , -- immediately after "bromides".
Lines 29, 32, 34, 44, 48, 58, 61 and 64, delete "-" after "1".

Signed and Sealed this

Third Day of September, 2002

Attest:

Attesting Officer

JAMES E. ROGAN
Director of the United States Patent and Trademark Office